(12) United States Patent
Knott et al.

(10) Patent No.: US 9,353,225 B2
(45) Date of Patent: May 31, 2016

(54) COMPOUNDS HAVING GUANIDINE GROUPS AND CONTAINING SEMI-ORGANIC SILICON GROUPS

(71) Applicant: Evonik Degussa GmbH, Essen (DE)

(72) Inventors: Wilfried Knott, Essen (DE); Michael Ferenz, Essen (DE); Michael Fiedel, Essen (DE); Wolfgang Hojak, Essen (DE); Bastian Matthias Brugger, Oberhausen (DE); Frank Schubert, Neukirchen-Vluyn (DE); Anke Lewin, Dusseldorf (DE)

(73) Assignee: Evonik DeGussa GmbH, Essen (DE)

( * ) Notice: Subject to any disclaimer, the term of this patent is extended or adjusted under 35 U.S.C. 154(b) by 0 days.

(21) Appl. No.: 14/457,933

(22) Filed: Aug. 12, 2014

(65) Prior Publication Data

US 2015/0057412 A1 Feb. 26, 2015

(30) Foreign Application Priority Data

Aug. 23, 2013 (DE) .......................... 10 2013 216 787

(51) Int. Cl.
| | | |
|---|---|---|
| *C08G 77/08* | (2006.01) | |
| *C07F 7/21* | (2006.01) | |
| *C07F 7/10* | (2006.01) | |
| *C09D 183/04* | (2006.01) | |
| *C09D 183/08* | (2006.01) | |
| *C09J 183/08* | (2006.01) | |
| *C08G 77/388* | (2006.01) | |
| *C08G 77/26* | (2006.01) | |

(52) U.S. Cl.
CPC . *C08G 77/08* (2013.01); *C07F 7/10* (2013.01); *C07F 7/21* (2013.01); *C09D 183/04* (2013.01); *C09D 183/08* (2013.01); *C09J 183/08* (2013.01); *C08G 77/26* (2013.01); *C08G 77/388* (2013.01)

(58) Field of Classification Search
None
See application file for complete search history.

(56) References Cited

U.S. PATENT DOCUMENTS

| | | | |
|---|---|---|---|
| 3,201,071 A | 8/1965 | Siebenthal | |
| 3,388,079 A | 6/1968 | Vandenberg | |
| 4,180,642 A * | 12/1979 | Takago | 528/32 |
| 4,248,992 A | 2/1981 | Takago | |
| 4,339,563 A * | 7/1982 | Takago et al. | 528/14 |
| 4,579,963 A * | 4/1986 | Arai et al. | 556/423 |
| 4,721,766 A * | 1/1988 | Inoue et al. | 528/18 |
| 4,734,479 A * | 3/1988 | Inoue et al. | 528/18 |
| 5,097,053 A * | 3/1992 | Baghdachi et al. | 556/420 |
| 5,180,771 A * | 1/1993 | Arai et al. | 524/588 |
| 5,239,100 A * | 8/1993 | Tsunetoshi et al. | 556/417 |
| 5,371,161 A | 12/1994 | Knott | |
| 5,455,367 A | 10/1995 | Klein et al. | |
| 5,475,127 A | 12/1995 | Klein et al. | |
| 5,705,590 A | 1/1998 | Suzuki et al. | |
| 5,840,806 A | 11/1998 | Komazaki et al. | |
| 5,880,245 A | 3/1999 | Fujita et al. | |
| 5,968,681 A | 10/1999 | Miura et al. | |
| 6,159,389 A | 12/2000 | Miura et al. | |
| 6,162,563 A | 12/2000 | Miura et al. | |
| 6,291,622 B1 | 9/2001 | Drose et al. | |
| 6,307,082 B1 | 10/2001 | Klein et al. | |
| 6,541,593 B1 | 4/2003 | Jyono et al. | |
| 6,703,442 B1 | 3/2004 | Ando et al. | |
| 6,740,725 B2 * | 5/2004 | Horikoshi et al. | 528/21 |
| 6,858,663 B2 | 2/2005 | Knott et al. | |
| 7,018,458 B2 | 3/2006 | Knott et al. | |
| 7,053,135 B2 | 5/2006 | Schaub et al. | |
| 7,115,695 B2 | 10/2006 | Okamoto et al. | |
| 7,125,585 B2 | 10/2006 | Dudzik et al. | |
| 7,196,153 B2 | 3/2007 | Burkhart et al. | |
| 7,365,145 B2 | 4/2008 | Yang et al. | |
| 7,598,334 B2 | 10/2009 | Ferenz et al. | |
| 7,605,203 B2 | 10/2009 | Feng et al. | |
| 7,605,284 B2 | 10/2009 | Brueckner et al. | |
| 7,612,158 B2 | 11/2009 | Burkhart et al. | |
| 7,612,159 B2 | 11/2009 | Burkhart et al. | |
| 7,619,035 B2 | 11/2009 | Henning et al. | |
| 7,635,581 B2 | 12/2009 | Ferenz et al. | |
| 7,645,848 B2 | 1/2010 | Knott et al. | |
| 7,727,599 B2 | 6/2010 | Doehler et al. | |
| 7,754,778 B2 | 7/2010 | Knott et al. | |
| 7,825,205 B2 | 11/2010 | Knott et al. | |
| 7,825,206 B2 | 11/2010 | Neumann et al. | |
| 7,825,207 B2 | 11/2010 | Ferenz et al. | |

(Continued)

FOREIGN PATENT DOCUMENTS

| | | |
|---|---|---|
| DE | 10319303 A1 | 12/2004 |
| DE | 102004045358 A1 | 4/2006 |

(Continued)

OTHER PUBLICATIONS

Noll W.; "Chemie and Technologie der Silicone" Wiley-VCH Verlag GmbH & Co. KGaA, Weinheim, 1960, p. 161 ff.
Alwyn Davis; "Organotin compounds in technology and industry", Journal of Chemical Research, 4, 2010, p. 186, ISBN 0308-2342.
Alwyn G. Davies "Organotin Chemistry", 2004, Wiley-VCH, ISBN 3-527-31023-1, p. 383.
Frederick Kurzer, K. Douragh-Zader; "Advances in the Chemistry of Carbodiimides" Chemical Reviews, vol. 67, No. 2, 1967, p. 99 ff.
Henri Ulrich; "Chemistry and Technology of Carbodiimides"; John Wiley & Sons Ltd., ISBN 978-0-470-06510-5, 2007.
Organische Chemie: Grundlagen, Stoffklassen, Reaktionen, Konzepte, Molekülstruktur (Eberhard Breitmaier, Günther Jung; Thieme Verlag, 2009, 6th. Edn., section 25.7.1).
Xuehua Zhu, Zhu Du, Fan Xu and Qi Shen; J. Org. Chem. 2009, 74, 6347-6349.

*Primary Examiner* — Robert S Loewe
(74) *Attorney, Agent, or Firm* — Frommer Lawrence & Haug LLP

(57) ABSTRACT

This invention relates to compounds having guanidine groups and containing semi-organic silicon groups, their use for the curing of compounds containing alkoxysilyl groups, compositions comprising the curing catalysts of the invention, and use of the compositions as adhesives and sealants and also as coating materials.

15 Claims, No Drawings

(56) References Cited

U.S. PATENT DOCUMENTS

| | | | |
|---|---|---|---|
| 7,825,209 | B2 | 11/2010 | Knott et al. |
| 7,834,122 | B2 | 11/2010 | Ferenz et al. |
| 7,855,265 | B2 | 12/2010 | Thum et al. |
| 7,964,694 | B2 | 6/2011 | Ferenz et al. |
| 8,138,294 | B2 | 3/2012 | Henning et al. |
| 8,247,525 | B2 | 8/2012 | Schubert et al. |
| 8,283,422 | B2 | 10/2012 | Schubert et al. |
| 8,309,664 | B2 | 11/2012 | Knott et al. |
| 8,309,673 | B2 | 11/2012 | Schubert et al. |
| 8,334,355 | B2 | 12/2012 | Henning et al. |
| 8,420,567 | B1 | 4/2013 | Naumann et al. |
| 8,420,748 | B2 | 4/2013 | Henning et al. |
| 8,455,603 | B2 | 6/2013 | Ferenz et al. |
| 8,466,248 | B2 | 6/2013 | Meyer et al. |
| 8,476,189 | B1 | 7/2013 | Naumann et al. |
| 8,557,944 | B2 | 10/2013 | Henning et al. |
| 8,598,295 | B2 | 12/2013 | Henning et al. |
| 8,609,798 | B2 | 12/2013 | Knott et al. |
| 8,617,529 | B2 | 12/2013 | Herrwerth et al. |
| 8,623,984 | B2 | 1/2014 | Henning et al. |
| 8,685,376 | B2 | 4/2014 | Czech et al. |
| 8,722,834 | B2 | 5/2014 | Knott et al. |
| 8,722,836 | B2 | 5/2014 | Knott et al. |
| 8,729,207 | B2 | 5/2014 | Hartung et al. |
| 8,772,423 | B2 | 7/2014 | de Gans et al. |
| 8,779,079 | B2 | 7/2014 | Henning et al. |
| 2002/0016418 | A1 | 2/2002 | Maruyama et al. |
| 2002/0115811 | A1 | 8/2002 | Huang et al. |
| 2002/0161158 | A1 | 10/2002 | Burkhart et al. |
| 2003/0110947 | A1 | 6/2003 | Kita et al. |
| 2003/0124432 | A1 | 7/2003 | Miura et al. |
| 2005/0113547 | A1 | 5/2005 | Li et al. |
| 2006/0155090 | A1 | 7/2006 | Ferenz |
| 2006/0241249 | A1 | 10/2006 | Kasai et al. |
| 2007/0066768 | A1 | 3/2007 | Gauthier et al. |
| 2007/0128143 | A1 | 6/2007 | Gruning et al. |
| 2007/0179236 | A1 | 8/2007 | Landon |
| 2007/0197678 | A1 | 8/2007 | Cavaleiro et al. |
| 2008/0111103 | A1 | 5/2008 | Heitner |
| 2008/0312369 | A1 | 12/2008 | Beers et al. |
| 2009/0005498 | A1 | 1/2009 | Lin et al. |
| 2009/0182091 | A1 | 7/2009 | Noro et al. |
| 2010/0004367 | A1 | 1/2010 | Yano et al. |
| 2010/0022435 | A1 | 1/2010 | Henning et al. |
| 2010/0034765 | A1 | 2/2010 | Herrwerth et al. |
| 2010/0041910 | A1 | 2/2010 | Schubert et al. |
| 2010/0068534 | A1 | 3/2010 | Paul et al. |
| 2010/0081781 | A1 | 4/2010 | Schubert et al. |
| 2010/0152373 | A1 | 6/2010 | Wakabayashi et al. |
| 2010/0248325 | A1 | 9/2010 | Eckstein et al. |
| 2011/0040033 | A1 | 2/2011 | Maliverney et al. |
| 2011/0042004 | A1 | 2/2011 | Schubert et al. |
| 2011/0046299 | A1* | 2/2011 | Maliverney et al. .......... 524/588 |
| 2011/0046305 | A1 | 2/2011 | Schubert et al. |
| 2011/0154772 | A1 | 6/2011 | Lontchar et al. |
| 2011/0232825 | A1 | 9/2011 | Mack et al. |
| 2011/0251070 | A1 | 10/2011 | Poffenberger et al. |
| 2011/0288245 | A1 | 11/2011 | Roscher et al. |
| 2011/0301254 | A1 | 12/2011 | Knott et al. |
| 2012/0022210 | A1 | 1/2012 | Davio et al. |
| 2012/0027704 | A1 | 2/2012 | Henning et al. |
| 2012/0028022 | A1 | 2/2012 | Brugger et al. |
| 2012/0029090 | A1 | 2/2012 | Brugger et al. |
| 2012/0065308 | A1 | 3/2012 | Sumi et al. |
| 2012/0067520 | A1 | 3/2012 | Schubert et al. |
| 2012/0068110 | A1 | 3/2012 | Schubert et al. |
| 2012/0168664 | A1 | 7/2012 | Maurer et al. |
| 2012/0190760 | A1 | 7/2012 | Henning et al. |
| 2012/0279922 | A1 | 11/2012 | Haensel et al. |
| 2012/0282210 | A1 | 11/2012 | Henning et al. |
| 2012/0294819 | A1 | 11/2012 | Herrwerth et al. |
| 2012/0308494 | A1 | 12/2012 | Schubert et al. |
| 2013/0035408 | A1 | 2/2013 | Knott et al. |
| 2013/0035409 | A1 | 2/2013 | Hubel et al. |
| 2013/0041115 | A1 | 2/2013 | Knott et al. |
| 2013/0213267 | A1 | 8/2013 | Fiedel et al. |
| 2013/0217907 | A1 | 8/2013 | Henning et al. |
| 2013/0217930 | A1 | 8/2013 | Haensel et al. |
| 2013/0259821 | A1 | 10/2013 | Henning et al. |
| 2013/0331592 | A1 | 12/2013 | Hartung et al. |
| 2014/0094532 | A1 | 4/2014 | Knott et al. |

FOREIGN PATENT DOCUMENTS

| | | |
|---|---|---|
| DE | 202006010035 U1 | 9/2006 |
| DE | 102006060357 A1 | 7/2007 |
| EP | 0459300 A2 | 12/1991 |
| EP | 0819749 A2 | 1/1998 |
| EP | 0885913 A1 | 12/1998 |
| EP | 1081191 A2 | 3/2001 |
| EP | 1146062 A1 | 10/2001 |
| EP | 1229092 A2 | 8/2002 |
| EP | 1264854 A1 | 12/2002 |
| EP | 1380625 A1 | 1/2004 |
| EP | 1445287 A1 | 8/2004 |
| EP | 1457527 A1 | 9/2004 |
| EP | 1563822 A2 | 8/2005 |
| EP | 1614717 A1 | 1/2006 |
| EP | 1650257 A1 | 4/2006 |
| EP | 1738737 A1 | 1/2007 |
| EP | 1844106 A1 | 10/2007 |
| EP | 1867693 A1 | 12/2007 |
| EP | 1985666 A1 | 10/2008 |
| EP | 2003155 A1 | 12/2008 |
| EP | 2036944 A1 | 3/2009 |
| EP | 2093244 A1 | 8/2009 |
| EP | 2119745 A1 | 11/2009 |
| EP | 2123720 A1 | 11/2009 |
| EP | 2182031 A1 | 5/2010 |
| EP | 2267083 A1 | 12/2010 |
| EP | 2289988 A1 | 3/2011 |
| EP | 2289997 A1 | 3/2011 |
| EP | 2338938 A1 | 6/2011 |
| EP | 2386287 A2 | 11/2011 |
| EP | 2388297 A1 | 11/2011 |
| EP | 2415797 A1 | 2/2012 |
| JP | 2004043738 A | 2/2004 |
| JP | 2006052353 A | 2/2006 |
| WO | WO-00/37533 A1 | 6/2000 |
| WO | WO-00/56817 A1 | 9/2000 |
| WO | WO-02/34838 A1 | 5/2002 |
| WO | WO-02/53664 A2 | 7/2002 |
| WO | WO-03/006534 A1 | 1/2003 |
| WO | WO-2005/078036 A1 | 8/2005 |
| WO | WO-2005/100482 A1 | 10/2005 |
| WO | WO-2006/134995 A1 | 12/2006 |
| WO | WO-2008/001784 A1 | 1/2008 |
| WO | WO-2008/014224 A2 | 1/2008 |
| WO | WO-2008/064872 A2 | 6/2008 |
| WO | WO-2008/133265 A1 | 11/2008 |
| WO | WO-2009/020040 A1 | 2/2009 |
| WO | WO-2009/022743 A1 | 2/2009 |
| WO | WO-2009/106720 A1 | 9/2009 |
| WO | WO-2009/145245 A1 | 12/2009 |
| WO | WO-2010/070666 A1 | 6/2010 |
| WO | WO-2010/070894 A1 | 6/2010 |
| WO | WO-2010/086299 A1 | 8/2010 |
| WO | WO-2010/117744 A2 | 10/2010 |
| WO | WO-2011/003291 A1 | 1/2011 |
| WO | WO-2011/014273 A1 | 2/2011 |
| WO | WO-2011/026658 A1 | 3/2011 |
| WO | WO-2011/046235 A1 | 4/2011 |
| WO | WO-2011/054782 A1 | 5/2011 |
| WO | WO-2011/080034 A2 | 7/2011 |
| WO | WO-2011/095261 A1 | 8/2011 |
| WO | WO-2012/020560 A1 | 2/2012 |
| WO | WO 2012/076293 A2 | 6/2012 |
| WO | WO-2012/081483 A1 | 6/2012 |
| WO | WO-2012/084760 A1 | 6/2012 |
| WO | WO-2012/084762 A1 | 6/2012 |
| WO | WO-2012/095826 A2 | 7/2012 |
| WO | WO-2012/098115 A1 | 7/2012 |

\* cited by examiner

COMPOUNDS HAVING GUANIDINE GROUPS AND CONTAINING SEMI-ORGANIC SILICON GROUPS

The present application claims priority from German Patent Application No. DE 10 2013 216 787.3 filed on Aug. 23, 2013, the disclosure of which is incorporated herein by reference in its entirety.

FIELD OF THE INVENTION

This invention relates to compounds having guanidine groups and containing semi-organic silicon groups, their use for the curing of compounds containing alkoxysilyl groups, compositions comprising the curing catalysts of the invention, and use of the compositions as adhesives and sealants and also as coating materials.

Within the scope of the invention "compounds containing semi-organic silicon groups" means that the stated compounds have at least one siloxane unit, and therefore have at least one Si—O—Si unit. The stated compounds containing semi-organic silicon groups preferably have a siloxane framework, which accordingly has a plurality of alternating silicon atoms and oxygen atoms. Regarding the definitional classification of such compounds as semi-organic compounds, reference may be made to the encyclopaedic Römpp-Lexikon (entry heading: Polyorganosiloxane/Silicone).

Catalysts suitable for the curing of monomers, oligomers or polymers that carry alkoxysilyl groups include in principle all those catalysts which promote both the hydrolysis of the alkoxy function and/or the condensation of the silanols formed therefrom. Very early descriptions of suitable compounds are found in W. Noll—"Chemie and Technologie der Silicone" (Wiley-VCH Verlag GmbH & Co. KGaA, Weinheim, 1960, p. 161 ff).

Polymers which carry trialkoxysilyl groups can be prepared by a variety of reactions; known accordingly are not only alkoxysilyl-bearing polyurethanes, polyesters, polyethers, polyacylates or the like, but also other rubbers and/or further polymers. Also known are polymers which carry the silanols (R1R2R3-Si—OH) that are obtainable from the hydrolysis of alkoxy functions. Such compounds may in turn be silane-based or else may have a pronounced inorganic polymer character, as in the case of the poly(dimethyl)siloxanols (PDM siloxanes), for example.

As the skilled person is aware, the hydrolysis and condensation reaction of trialkoxysilyl functions experiences a maximum within the strongly acidic pH range, and in the strongly alkaline pH range. Besides the strong (Lewis) acids and bases, however, other (metal) compounds as well are known to promote the hydrolysis/condensation, but to date their precise catalytic mechanism has not been adequately elucidated.

WO 2009/106720 (US 2011/040033) discloses metal sulphonates and metal fluoroalkylsulphonates as polycondensation catalysts, which cure organopolysiloxane compositions to give siloxane elastomers. A great disadvantage of such catalysts is that as well as having a restricted availability and a high price, they cannot be used in the presence of basic components such as amines or basic fillers (e.g. chalks). The latter are employed especially in formulations within the adhesives and sealants sector.

The same applies to strongly Lewis-acidic catalysts such as, for example, boron halides, metal halides such as $AlCl_3$, $TiCl_4$, $ZrCl_4$, $SnCl_4$, $FeCl_2$, $FeCl_3$, $ZnCl_2$ and their amine complexes, which are claimed in EP 2119745 (US 2010/152373) and whose toxicological profile appears likewise to be objectionable.

Less toxicologically objectionable catalyst preparations, such as metal carboxylates in combination with amine compounds, for example, of the kind described in EP 1445287 (U.S. Pat. No. 7,115,695), for example, exhibit an inadequate rate of curing of the binder matrix, of up to 5 days. Cure times of this duration are generally unacceptable for the great majority of applications.

The use of curing catalysts based on titanates or titanium complexes appeared promising, but these catalysts exhibited strong yellowing of the curing compositions and also, in some cases, showed incompatibilities with other amine components present in the curing composition.

Good curing results without the unwanted side effects described are displayed by organotin compounds. These compounds are well known to the skilled person from the prior art (Alwyn Davis—"Organotin compounds in technology and industry", Journal of Chemical Research, 4, 2010, p. 186, ISBN 0308-2342 and Alwyn G. Davies "Organotin Chemistry", 2004, Wiley-VCH, ISBN 3-527-31023-1, p. 383), but are coming under increasing criticism from a toxicological standpoint. The use of organotin compounds is therefore highly debated, not least in view of the restrictions placed on them by the amendment to the EU Directive 76/769 EEC of 28 May 2009. Examples of the use of organotin compounds are found in patents including DE 103 19 303 and DE 10 2006 060 357, wherein catalysis by means of dibutyltin and/or dioctyltin compounds is employed for the curing of poly(dimethylsiloxane) compounds (PDM compounds).

It is therefore likely that tin salts as well will be considered more critically from a toxicological standpoint in the future. In principle, tin carboxylates are also suitable for use as curing catalysts, as shown by WO 0056817 (U.S. Pat. No. 6,703,442).

WO 2010/086299 (US 2011288245) describes moisture-crosslinking reaction mixtures which contain polymers that carry trialkoxysilyl groups, and which are cured by means of niobium compounds and tantalum compounds. Such catalysts are considered uneconomical, since their availability on the world market is limited and the price of the raw material is very high. Similar comments apply to the use of hafnium alkoxides and germanium alkoxides, as described in JP 2004043738 and JP 2006052353, respectively.

Catalysts which promote the curing of alkoxysilyl groups are well known to the skilled person. The following examples may be given: tin compounds such as tin diacetate, tin dioctoate, dibutyltin diacetylacetonate, dibutyltin dilaurate, tin tetraacetate, dibutyltin diacetate, dibutyltin dioctoate, dibutyltin dilaurate, dibutyltin dioleate, dimethoxydibutyltin, dimethyltin, dibutyltin benzylmaleate, bis(triethoxysiloxy)dibutyltin, diphenyltin diacetate, titanium compounds, such as tetraethoxytitanium, tetra-n-propoxytitanium, tetraisopropoxytitanium, tetra-n-butoxytitanium, tetraisobutoxy-titanium, tetrakis(2-ethylhexoxy)titanium, diisopropoxybis(ethylacetoacetato)titanium, dipropoxybis(acetylacetonato)titanium, diisopropoxybis(acetylacetonato)titanium, dibutoxybis(acetylacetonato)titanium, triisopropoxyallyltitanium acetate, isopropoxyoctylene glycol or bis(acetylacetonato)titanium oxide, metallo-aliphatic compounds, such as lead diacetate, lead di-2-ethylhexanoate, lead dineodecanoate, lead tetraacetate, lead tetrapropionate, zinc acetylacetonate, zinc 2-ethylcaproate, zinc diacetate, bis(2-ethylhexanoyl)zinc, zinc dineodecanoate, zinc diundecenoate, zinc dimethacrylate, tetrakis(2-ethylhexanoyl)zirconium dichloride, tetrakis(methacryloyl)zirconium dichloride, and cobalt diacetate. Furthermore, use may also be made of bismuth catalysts, iron(II) and iron(III) compounds, e.g. iron(III) acetylacetonate or iron diacetate, aluminium compounds, e.g. aluminium acetylacetonate, calcium compounds, e.g. calcium ethylenediaminetetraacetate, and magnesium compounds, e.g. magnesium ethylenediaminetetraacetate.

Amines as well are used, such as, for example, triethylamine, tributylamine, aminopropyltrimethoxysilane, N-(2-aminoethyl)-3-aminopropyltrimethoxysilane, tetra-methylguanidine or 1,8-diazabicyclo[5.4.0]-7-undecene, 1,4-diazabicyclo[2.2.2]octane, 1,5-diazabicyclo[4.3.0]non-5-ene, N,N-bis(N,N-dimethyl-2-aminoethyl)methylamine, N,N-dimethylcyclohexylamine, N,N-dimethylphenylamine, N-ethylmorpholine, etc., and/or their mineral, Brønsted, Lewis or carboxylic acid salts. Likewise catalytically active are tetraalkylammonium compounds such as N,N,N-trimethyl-N-2-hydroxypropylammonium hydroxide, N,N,N-trimethyl-N-2-hydroxypropylammonium 2-ethylhexanoate or choline 2-ethylhexanoate. Organic or inorganic Brønsted acids as well, such as methanesulphonic acid, p-toluenesulphonic acid, dodecylbenzenesulphonic acid, 1-naphthalenesulphonic acid, camphorsulphonic acid, acetic acid, trifluoroacetic acid or benzoyl chloride, hydrochloric acid, phosphoric acid, the monoesters and/or diesters thereof, such as, for example, butyl phosphate, (iso)propyl phosphate, dibutyl phosphate etc., are suitable as catalysts. Inorganic and organic Brønsted bases as well, such as sodium hydroxide, tetramethylammonium hydroxide, potassium hydroxide or tetrabutylammonium hydroxide, for example, are suitable as catalysts. It is of course also possible to employ combinations of two or more catalysts.

Also known as curing catalysts are the so called photolatent bases, of the kind described in WO 2005/100482. Photolatent bases are preferably organic bases having one or more basic nitrogen atoms, which initially are present in a blocked form and which release the basic form only on irradiation with UV light, visible light or IR radiation, through splitting of the molecule.

Also catalytically active are catalysts which are sold by Du Pont under the trade name Tyzor®. The same applies to catalysts of the Kenreact® (Kenrich), Borchi Kat® (Borchers) and K-Cure®/Nacure® (King Industries) types.

WO 2010/117744 (US 2012022210) discloses the use of superbasic phosphazene catalysts for the condensation of PDM-OH siloxanes. However, they display an unfavourable toxicological profile, are uneconomic, and in a multiplicity of applications they therefore cannot be used or require laborious separation and/or aftertreatment.

A strongly basic nitrogen moiety, the function known as the guanidine function occurs frequently in nature, in the form of the amino acid arginine, for example. One simple access route to guanidine structures is the reaction of nitrogen compounds such as ammonia, amines or amine derivatives with carbodiimides, which contain the structural feature of an R—N=C=N—R moiety. Such carbodiimides are readily available commercially, in the form of cyanamide, N,N-dicyclohexylcarbodiimide, bisisopropylcarbodiimide, N-(3-dimethylaminopropyl)-N'-ethylcarbodiimide hydrochlorides, 1,3-di-p-tolylcarbodiimide and other carbodiimide derivatives, for example.

The reactive diversity of the carbodiimides is known to the skilled person and comprehensively described in the literature, as is the reaction with nucleophiles such as, for example, oxygen-containing or nitrogen-containing groups. Such reactions are found, for example, in Frederick Kurzer, K. Douragh-Zader—"Advances in the Chemistry of Carbodiimides" (Chemical Reviews, Vol. 67, No. 2, 1967, p. 99 ff.) and in Henri Ulrich—"Chemistry and Technology of Carbodiimides" (John Wiley & Sons Ltd., ISBN 978-0-470-06510-5, 2007).

The preparation of guanidine structures is possible through the reaction of amines and carbodiimides with catalysis by ytterbium trifluoromethanesulphonate (Yb(OTf)$_3$), leading, in the case of the reaction of primary amines, to a selective 1,3 hydrogen migration. It is also possible to carry out the reaction using other metal triflates, such as lanthanum, neodymium, samarium, europium or erbium. The reaction described by Qi Shen et al. may be conducted, moreover, under very mild reaction conditions to give high product yields (J. Org. Chem. 2009, 74, 6347-6349); the cited document is fully part of the present invention.

Guanidine structures are also obtainable through the substitution of compounds which carry haloalkyl groups with guanidines such as tetramethyl guanidine, for example. Such substitution on a chloropropylsilane is described in U.S. Pat. No. 4,248,992, for example.

An access route to semi-organic-polymeric guanidine structures is disclosed by EP 1 844 106 B (U.S. Pat. No. 7,825,207). By ring opening of epoxy-functional siloxanes through guanidine compounds which carry amino groups, guanidine-functional siloxanes are obtainable, and are suitable for use in cosmetic formulations, for example.

EP 1985666 (US 2009/182091) describes amidines and EP 2123720 (US 2010/004367) guanidines having organic radicals for the curing of polyethers which carry silyl groups terminally. Despite the organic modification, which ought to make them more compatible in the polymer matrix to be cured, the organic, low molecular mass guanidine derivates used in these applications exhibit inadequate curing kinetics and/or must be dissolved or dispersed, at cost and inconvenience, in a preceding processing step. The catalyst preparations thus prepared are difficult to incorporate as well, on account of their dispersion character, and this presents significant performance disadvantages. The auxiliaries used and also the catalysts are migratable in the end products, meaning that they may diffuse to the surface (known as "exudation") and adversely alter this surface. These alterations lead, for example, to a change in the tactile sensation, and particularly in the case of sealants they lead to formation of a surface film which in turn results, for example, in increased soiling of the filled sealing joint.

It is general knowledge to the skilled person that polyethers containing oxypropylene are not infinitely miscible with silanes and/or siloxanes. It can therefore be assumed that silyl modification on the catalytically active guanidine function will lead to a deterioration in the compatibility in a polyether and hence to a reduced curing rate. In continuation of this concept, it may further be expected that semi-organic polydimethylsiloxane derivatives with guanidine functions will likewise have this disadvantage, or will exhibit it even more strongly.

Since a silane or siloxane group is highly compatible with siloxanes, it is not surprising that, as shown in EP 2182031 as well, it is possible to cure siloxanes carrying alkoxysilyl end groups using curing catalysts based on silanes carrying tetramethyl guanidine groups.

Many of the approaches described in the prior art to the catalysis of alkoxysilyl compounds are notable for unwanted qualities, and so hinder a broad applicability. Hence they are uneconomic, exhibit insufficient curing rates, display unwanted migration effects leading to a poor surface image of the curing compositions, or are toxicologically objectionable.

There was therefore a need for catalysts which do not have the deficiencies described above.

It is noted that citation or identification of any document in this application is not an admission that such document is available as prior art to the present invention.

It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

OBJECT OF THE INVENTION

It is an object of the present invention, therefore, to find heavy-metal-free or entirely metal-free curing catalysts which accelerate the curing of compounds containing alkoxysilyl groups and to overcome at least one of the disadvantages of the prior art.

SUMMARY OF THE INVENTION

Surprisingly it has been found that this object was able to be achieved by means of compounds having guanidine groups and containing semi-organic silicon groups.

Subject matter of the present invention are therefore compounds having guanidine groups and containing semi-organic silicon groups, these compounds being described below.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

An advantage of the compounds having guanidine groups and containing semi-organic silicon groups, or siloxanes having guanidine groups, is their high storage stability.

Likewise subject matter of the present invention is the use of compounds having guanidine groups and containing semi-organic silicon groups as curing catalysts for compounds containing alkoxysilyl groups.

An advantage of the inventive use of compounds having guanidine groups and containing semi-organic silicon groups as curing catalysts is that the mechanical properties of the products exhibit just a little or no dependency over a wide concentration range of the catalyst in the composition.

A further advantage of the inventive use is high product safety.

Another advantage of the inventive use is a better toxicological compatibility by comparison with other catalyst systems known in the prior art.

A further subject of the present invention are compositions comprising component (a) at least one compound having guanidine groups and containing semi-organic silicon groups, and component (b) at least one compound containing alkoxysilyl groups.

The compositions of the invention have the advantage that in the curing of compounds containing alkoxysilyl groups they exhibit significantly better curing outcomes by comparison with organically modified guanidine derivatives and also exhibit other significant performance advantages.

A further subject of the present invention is a method for curing compounds containing alkoxysilyl groups, in which the compounds of the invention having guanidine groups and containing semi-organic silicon groups lead to the curing of the polymers containing alkoxysilyl groups, to form Si—O—Si bonds.

The method of the invention is advantageous since no metal catalysts are added for the curing.

The method is also advantageous because the curing is carried out at room temperature. The method is therefore more energy efficient.

The method of the invention is advantageous because no toxicologically objectionable metal compounds are added for the curing.

Preferred compounds of the invention having guanidine groups and containing semi-organic silicon groups are characterized in that the compounds containing semi-organic silicon groups are siloxanes.

The compounds having guanidine groups and containing semi-organic silicon groups, or siloxanes having guanidine groups, are preferably free of alkoxysilyl groups. This increases the storage stability.

More preferred compounds of the invention having guanidine groups and containing semi-organic silicon groups, or siloxanes having guanidine groups, are those of the formula (I)

$$M_a M^G_b D_c D^G_d T_e Q_f \tag{I}$$

a=0 to 10, preferably 0 to 5, more preferably greater than 0 to 4, especially preferably greater than 1 to less than 3, b=0 to 10, preferably 0 to 5, more preferably greater than 0 to 4, especially preferably greater than 1 to less than 3, c=0 to 350, preferably 1 to 150, more preferably greater than 1 to 15, very preferably 2 to 10, especially preferably greater than 2 to 5, d=0 to 50, preferably 1 to 25, more preferably greater than 1 to 10, very preferably 2 to 8, especially preferably greater than 2 to 5, e=0 to 50, preferably greater than 0 to 30, more preferably 0 to 10, very preferably greater than 1 to 5, especially preferably 2 to less than 4, f=0 to 10, preferably greater than 0 to 5, more preferably 0 to less than 5, especially preferably greater than 1 to less than 3, where the sum of the indices b and d is greater than or equal to 1 to 20, preferably greater than 1 to 15, especially preferably 2 to 10, with the proviso that when the index a is 2 and at the same time the sum of the indices b, c, e and f is zero, the index d is other than 1, or with the proviso that when the sum of the indices a, c, d, e and f is zero, the index b is greater than 1, preferably 2, especially preferably greater than 2, $M=[R_3SiO_{1/2}]$,
$M^G=[R^G R_2 SiO_{1/2}]$,
$D=[R_2SiO_{2/2}]$,
$D^G=[R^G R SiO_{2/2}]$,
$T=[RSiO_{3/2}]$,
$Q=[SiO_{4/2}]$, R are, independently of one another, identical or different and are $OR^a$ groups and/or linear or branched, saturated or else mono- or polyunsaturated hydrocarbon radicals, which may be interrupted by heteroatoms and/or may be substituted one or more times by hydroxyl, amino, carboxyl or aryl radicals, preferably being substituted by amino radicals, preferred hydrocarbon radicals, which may be optionally substituted by hydroxyl and amino radicals, are polyethers, alkyl radicals or aryl radicals, more preferably alkyl or aryl radicals, more preferably still alkyl radicals, especially methyl or propyl radicals, it being possible for the aryl radicals also to be substituted by $C_1$-$C_8$ alkyl radicals, $R^a$ is identical or different and is hydrogen and/or alkyl groups having 1 to 12 carbon atoms, more particularly methyl or ethyl, $R^G$ is a radical containing guanidine groups and of the formula (IIa), (IIb) or (IIc), the tautomers and/or salts thereof,

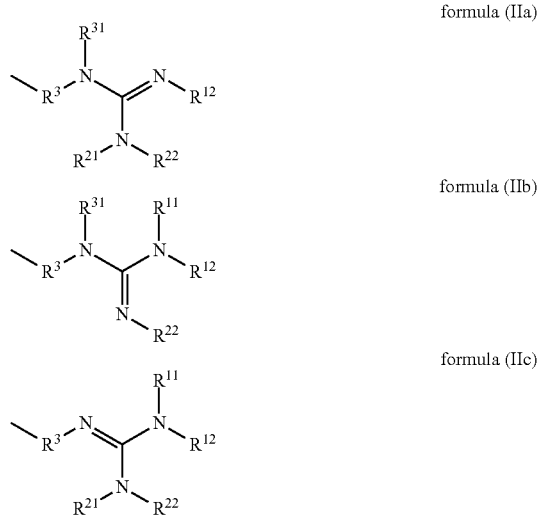

formula (IIa)

formula (IIb)

formula (IIc)

$R^3$ are divalent radicals which, independently of one another, are identical or different, linear or branched hydrocarbon radicals containing 1 to 50 carbon atoms, preferably 2 to 20, more preferably 3 to 10, especially preferably more than 3 to 8, which may be interrupted by heteroatoms, preferred heteroatoms being oxygen, nitrogen or sulphur, and/or which may be substituted one or more times by hydroxyl or amino radicals, more preferably the hydrocarbon radical is a propylene radical;

$R^{11}$, $R^{12}$, $R^{21}$, $R^{22}$ and $R^{31}$ are, independently of one another, identical or different and are hydrogen, linear or branched or cyclic hydrocarbons containing 1 to 15 carbon atoms, preferably more than 1 to 10, especially 2 to 7, it also being possible for the hydrocarbons to contain 1 or 2 heteroatoms, preferred heteroatoms being nitrogen, oxygen and silicon.

In particularly preferred siloxanes having guanidine groups are represented by the formula (I), the radicals $R^{11}$, $R^{12}$, $R^{21}$, and $R^{22}$ in $R^G$ of the formula (IIc) are all hydrogen or methyl, more preferably all methyl.

In additionally particularly preferred siloxanes of the formula (I) having guanidine groups, the radicals $R^{12}$ and $R^{22}$ in the formula (IIc) are identical only in the event that the radicals $R^{11}$ and $R^{21}$ are both hydrogen and $R^{31}$ is not present.

Preferred radicals $R^{11}$, $R^{12}$, $R^{21}$ and $R^{22}$ in the formula (IIc) are methyl, ethyl, propyl, isopropyl, butyl, tert-butyl, cyclohexyl, phenyl, 4-nitrophenyl, p-tolyl, trimethylsilyl, 2-morpholinoethyl, 3-dimethylaminopropyl or hydrogen. Particularly preferred radicals are ethyl, isopropyl or cyclohexyl, especially preferably methyl and cyclohexyl.

Additionally preferably the radicals $R^{12}$ and $R^{22}$ in the formula (IIc) are identical.

More preferably the radicals $R^{12}$ and $R^{22}$ in the formula (IIc) are identical and are ethyl, isopropyl or cyclohexyl; especially preferably the radicals $R^{12}$ and $R^{22}$ are identical and are cyclohexyl.

Preference is given to siloxanes of formula (I) containing guanidine groups where the indices a, b, e and f adopt a value of zero, and the sum of the indices c+d is from 3 to 8, preferably greater than 3 to 6, more preferably 4 to less than 6, especially preferably 4 to 5.

Preference is given to siloxanes of formula (I) containing guanidine groups where the indices a, b, e and f adopt a value of zero, and the index d is 1 to 4, preferably greater than 1 to less than 4.

The different fragments of the compounds of the formula (I) may be distributed statistically.

The index numbers reproduced here and the value ranges for the indices indicated may be understood as average values of the possible statistical distribution of the structures and/or mixtures thereof that are actually present. This applies equally to structural formulae which as such are reproduced exactly per se, such as for formulae (I) and (III), for example.

Statistical distributions can be blockwise with any desired number of blocks and any desired sequence, or may be subject to a randomized distribution; they can also have an alternating structure or else form a gradient over the chain; in particular, they may also form all mixed forms in which optionally groups of different distributions can follow one another. Specific embodiments can lead to the statistical distributions experiencing limitations due to the embodiment. For all regions which are not affected by the limitation, the statistical distribution is not changed.

The guanidine groups according to the invention may be present in the form of tautomers, which may be expressed, for example, by the following formulae:

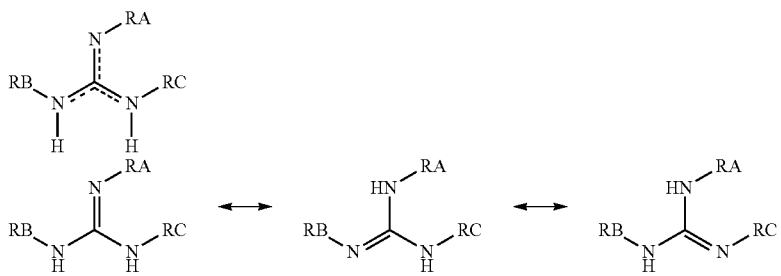

Included in particular are all mesomeric and tautomeric species and also radical species, as set out in, for example, "Organische Chemie: Grundlagen, Stoffklassen, Reaktionen, Konzepte, Molekülstruktur" (Eberhard Breitmaier, Günther Jung; Thieme Verlag, 2009, 6th. Edn., section 25.7.1).

In the above structures, preferably, one of the radicals, RA, RB or RC, represents the radical having siloxane groups from the formula (I).

All double bonds, even if they represent a preferred constitution, denote both E and Z configuration, or denote both cis and trans configuration.

The compounds having guanidine groups and containing semi-organic silicon groups may be positively charged through addition of acids, e.g. Brønsted or Lewis acids. In particular the guanidine groups may be positively charged. The addition of acids may be made stoichiometrically or sub-stoichiometrically in respect of the number of guanidine groups. In the case of sub-stoichiometric introduction, not all of the guanidine groups are positively charged.

Preferred Brønsted acids are mineral acids or carboxylic acids. Suitable mineral acids are hydrogen chloride acid or hydrochloric acid, sulphuric acid, phosphoric acid or nitric acid. Preferred carboxylic acids are aliphatic, saturated and unsaturated monocarboxylic, dicarboxylic and tricarboxylic acids.

Preferred Lewis acids are compounds of boron such as boranes, for example.

The word fragment "poly" in connection with this invention encompasses not only exclusively compounds having at least 3 repeating units of one or more monomers in the molecule, but also, more particularly, those compositions of compounds which exhibit a molecular weight distribution and possess an average molecular weight of at least 200 g/mol. This definition accounts for the circumstance that within the field of art in question it is common to identify such compounds as polymers even when they do not yet appear to satisfy the definition of a polymer as per OECD or REACH guidelines.

The compounds of the invention having guanidine groups and containing semi-organic silicon groups, and the siloxanes having guanidine groups, may be prepared in accordance with the techniques known from the prior art.

They are preferably prepared, for example, by substitution. For this purpose, siloxanes containing haloalkyl groups are reacted with guanidines. The guanidines are advantageously employed in excess. Unreacted quantities of guanidine are removed at the end of the reaction by means of thermal separation methods; one preferred thermal separation method is distillation.

Additionally preferred is the reaction of siloxanes containing aminoalkyl groups with carbodiimides such as, for example, diethylcarbodiimide, diisopropylcarbodiimide, methylpropylcarbodiimide, dicyclohexylcarbodiimide, hexamethylenecarbodiimide, heptamethylenecarbodiimide, 1-ethyl-3-(3-dimethylaminopropyl)carbodiimide, 1-cyclohexyl-3-(2-morpholinoethyl)carbodiimide meso-p-toluenesulphonate, 1-tert-butyl-3-(3-dimethylaminopropyl)carbodiimide, diphenylcarbodiimide, 4,4'-dinitrodiphenylcarbodiimide, di-p-tolylcarbodiimide and bis(trimethylsilyl)carbodiimide. The carbodiimides are used advantageously in amounts up to the stoichiometric equivalent; the ratio of carbodiimide to amino groups is preferably from 0.5 to 1, more preferably from 0.7 to 0.95, especially preferably from 0.75 to 0.85. Conversion figures in the examples are therefore based on the carbodiimides, which are used in possibly deficient proportions.

Use of the compounds of the invention having guanidine groups and containing semi-organic silicon groups for the curing of compounds containing alkoxysilyl groups.

The compounds containing alkoxysilyl groups are preferably compounds which are polymers containing alkoxysilyl groups.

More preferably the alkoxysilyl-containing compounds or polymers containing alkoxysilyl groups are the polymers of the formula (III)

$$P(SiX_wY_{(3-w)})_p \qquad (III)$$

where
P may be any desired polymer,
    preferably a polymer radical selected from a group consisting of alkyd resins, oil-modified alkyd resins, saturated or unsaturated polyesters, natural oils, epoxides, polyamides, polycarbonates, polyethylenes, polypropylenes, polybutylenes, polystyrenes, ethylene-propylene copolymers, (meth)acrylates, (meth)acrylamides and salts thereof, phenolic resins, polyoxymethylene homopolymers and copolymers, polyurethanes, polysulphones, polysulphide rubbers, nitrocelluloses, vinyl butyrates, vinyl polymers, ethylcelluloses, cellulose acetates and/or butyrates, rayon, shellac, waxes, ethylene copolymers, organic rubbers, polysiloxanes, polyethersiloxanes, silicone resins, polyethers, polyetheresters and/or polyether carbonates,
X independently at each occurrence is identical or different and is an alkoxy radical having 1 to 8 carbon atoms, preferably ethoxy and/or methoxy,
Y independently at each occurrence is identical or different and is an alkyl radical, preferably an alkyl radical having 1 to 20 carbon atoms, more preferably greater than 1 to 10 carbon atoms, and especially preferably 2 to 5 carbon atoms,
w independently at each occurrence is identical or different and is an index from 1 to 3, preferably greater than 1 up to 3, more preferably greater than 1 to less than 3,
p is 1 to 100, preferably greater than 1 to 50, more preferably 2 to 25, more preferably still greater than 2 to 10.

Preferred polymers containing alkoxysilyl groups or polymers of the formula (III) are polyethers.

Preferred polymers of the formula (III) containing alkoxysilyl groups comprise oxypropylene units. More preferably the polymers of the formula (III) comprise more than 50 wt % of oxypropylene units, based on the overall polymer molecule, more particularly more than 80 wt %.

Besides oxypropylene units, preferred polymers of the formula (III) containing alkoxysilyl groups comprise further heteroatoms apart from oxygen, these heteroatoms being selected preferably from nitrogen and sulphur, more particularly nitrogen. Still more preferred polymers of the formula (III) have nitrogen as part of the functional groups selected from amine group, amide group, thioamide group, carbamate group, thiocarbamate group, urethane group and thiourethane group, it being possible for a plurality of nitrogen atoms to be part of different functional groups.

Preferred polymers of the formula (III) containing alkoxysilyl groups have the alkoxysilyl groups in comb positions and/or terminally, based on the backbone of the polymer.

A feature of the compositions of the invention is that they comprise as component (a) the compounds of the invention having guanidine groups and containing semi-organic silicon groups, and as component (b) at least one compound containing alkoxysilyl groups.

As component (a), the compositions of the invention preferably comprise silanes or siloxanes containing guanidine groups, more preferably siloxanes. More preferably still, the siloxanes are those of the formula (I) as described above. With further preference the compositions of the invention comprise alkoxysilyl-containing polymers as component (b). More preferably the polymers are the polymers of the formula (III) as described above.

Additionally preferred are compositions of the invention which comprise the silanes or siloxanes of the invention containing guanidine groups, and also (b) at least one alkoxysilyl-containing polymer.

Additionally preferred are compositions of the invention which comprise the compounds of the formula (I) of the invention having guanidine groups and containing semi-organic silicon groups, and also (b) at least one alkoxysilyl-containing compound.

Further preferred are compositions of the invention which comprise the compounds of the invention having guanidine groups and containing semi-organic silicon groups, and also (b) at least one polymer of the formula (III) as described above.

Especially preferred are compositions of the invention which comprise the compounds of the formula (I) of the invention having guanidine groups and containing semi-organic silicon groups, and also (b) at least one alkoxysilyl-containing polymer of the formula (III) as described above.

Further preferred are the compositions of the invention in which component (a) is free of alkoxysilyl groups.

Examples in accordance with the invention of polymers containing alkoxysilyl groups are found in: WO2002/034838, US 2010/068534, WO 1996/033249, WO 2011/080034, EP1081191, U.S. Pat. No. 7,053,135, WO 2012/020560, WO 2010/070666, WO 2011/046235, EP2388297, WO 2010/070894, EP2338938, EP2289997, EP2267083, WO 2009/020040, WO 2008/133265, WO 2006/134995, US 2006/241249, U.S. Pat. No. 6,541,593, WO 2012/081483, EP1146062, EP1614717, WO 2011/032914, WO 2012/084762, WO 2012/084760, WO 2003/006534, WO 2011/026658, WO 2005/078036, US 2002/115811, US 2012/065308, US 2008/111103, US 2007/066768, U.S. Pat. No. 7,365,145, US 2007/179236, US 2009/005498, WO0037533, EP1264854, WO 2008/001784, WO 2009/022743, U.S. Pat. No. 5,840,806, EP1229092, WO 2002/053664, U.S. Pat. No. 5,968,681, EP0885913, U.S. Pat. No. 3,201,071, U.S. Pat. No. 6,159,389, U.S. Pat. No. 6,162,563, US 2003/124432, US 2003/110947, EP0819749, US 2011/154772, EP2289988, U.S. Pat. No. 5,705,590, EP2036944, WO 2011/054782, US 2011/232825, DE202006010035U, WO2008/014224, EP1738737, WO 2008/064872, DE102004045358, EP1563822, EP1650257, WO 2012/095826, EP1867693, US2005/113547, EP2003155, EP1380625, US2002016418, EP1457527, DE20201100010U, WO 2012/098115, WO 2009/145245, US 2008/312369, U.S. Pat. No. 7,605,203, EP2386287, U.S. Pat. No. 3,388,079, U.S. Pat. No. 5,880,245.

Especially preferred polymers containing alkoxysilyl groups as constituents of the compositions of the invention are those of the TEGOPAC® series (TEGOPAC is a trademark of Evonik Industries AG, Essen), those of the MS Polymer™ series (MS Polymer is a trademark of Kaneka, Japan), e.g. MS Polymer S203H, ~S303H, ~S227 and ~S327, those of the MS Silyl™ series (MS Silyl is a trademark of Kaneka), e.g. MS Silyl of sub-series ~SAT, e.g. with the specification ~010 (MS Silyl SAT010) and ~145, of the sub-series ~SAX, e.g. with the specification ~015 (MA Silyl SAX015), ~220, ~260, ~350, ~400, ~510, ~520, ~530, ~580 and ~590, of the sub-series ~MA, e.g. with the specification ~451 (MS Silyl MA451), ~850 and ~480, of the sub-series ~MAX, e.g. with the specification ~602 (MS Silyl MAX602), ~923 and ~951, those of the Desmoseal® series (Desmoseal is a trademark of Bayer MaterialScience, Germany), e.g. Desmoseal of the sub-series ~S XP with the specification ~2458 (Desmoseal S XP 2458), ~2636, ~2774 and ~2749, those of the Genioseal® series (Genioseal is a trademark of Wacker Chemie AG, Burghausen), e.g. Genioseal of the sub-series ~N, e.g. with the specification ~35 (Genioseal N35), ~35C, ~45, ~45-HAT, ~70 and ~70-HAT, of the sub-series ~WP, e.g. with the specification ~1 (Genioseal WP1) and ~2, of the sub-series XB, e.g. with the specification ~502 (Genioseal XB 502), of the sub-series ~STP-E, e.g. with the specification ~10 (Genioseal STP-E10), ~15, ~30 and ~35, those of the SPUR+ series (SPUR+ is a trademark of Momentive Performance Materials Inc., Leverkusen), e.g. SPUR+ 1015LM, ~1050MM, ~3100HM and ~3200HM, and those of the Polymer ST series from Evonik Industries AG, e.g. Polymer ST 47, ~48, ~61, ~61LV, ~75, ~77, ~80 and ~81.

The compositions of the invention may comprise further additives.

Preferred additions in the compositions of the invention may be selected from the group of diluents, co-catalysts, plasticizers, fillers, solvents, emulsifiers, adhesion promoters, rheological additives, additives for chemical drying, and/or stabilizers to counter thermal and/or chemical exposures and/or exposures through ultraviolet and visible light, thixotropic agents, flame retardants, blowing agents or defoamers, deaerating agents, film-forming polymers, antimicrobial and preservative substances, antioxidants, dyes, colorants and pigments, antifreeze agents, fungicides, reactive diluents, complexing agents, wetting agents, co-crosslinkers, spraying assistants, vitamins, growth substances, hormones, active pharmacological ingredients, fragrances, radical scavengers and/or other adjuvants.

More preferably the compositions comprise further additives as well as the components (a) and (b).

The compositions of the invention contain 0.5 to 4%, more particularly 1 to 2% of siloxanes of the invention containing guanidine groups, based on the total mass of all of the components in the composition.

The compositions of the invention are suitable preferably for the adhesive bonding and/or sealing of particulate or sheetlike substrates. A further possibility for service is use in the construction industry or in vehicle building, for the sealing and bonding of structural elements and components, and also for the coating of porous or non-porous, particulate or sheetlike substrates. The alkoxylation products that are used in this invention may be used outstandingly as the basis of a curable composition for the coating and modifying of surfaces and fibres. Further examples which may be given here are applications on metals, in that case in particular the construction materials such as iron, steel, stainless steel and cast iron, ferrous materials, aluminium, mineral substrates, such as stone, screeding, mortar and concrete, ceramics, glasses, ceramic materials, based in particular on solid metal oxides or non-metal oxides or carbides, aluminium oxide, magnesium oxide or calcium oxide, and also mineral substrates or organic substrates, polyesters, glass fibre-reinforced polyester, polyimide, textiles and fabrics made from cotton and polyester, cork and/or wood. The composition may likewise be utilized for binding, reinforcing and leveling uneven, porous or friable substrates, such as, for example, mineral substrates, chipboard and fibreboard panels made of wood or cork, composite materials such as, for example, wood composites such as MDF boards (medium-density fibreboards), WPC articles (wood plastic composites), chipboard panels, cork articles, laminated articles, ceramics, but also natural fibres and synthetic fibres.

As a result of this broad spectrum of adhesion, they are also suitable for the bonding of combinations of materials comprising the substrates stated. In this context it is not critical whether the surfaces are smooth or roughened or porous. Roughened or porous surfaces are preferred, on account of the greater area of contact with the adhesive.

The compositions of the invention are additionally preferably suitable for coating.

Application of the coating materials of the invention takes place in general by spray application, though they may also be applied by other application technologies such as, for example, brushing, rolling, flow coating, dipping, wiping and pouring.

The articles to be coated may have a smooth surface, or else may have non-uniform surfaces, as in the case of textiles, for example.

Suitable substrates include metallic substrates such as, for example, steel, cast steel, stainless steel, aluminium, cast aluminium or hot dip galvanized steel. For improved adhesion, the substrate may be roughened by sandblasting or sanding.

Non-metallic substrates as well may be employed, such as glass, ceramics and fabrics, more particularly textile fabrics.

The special product safety of the inventive use is characterized by protection against mismetering, more particularly overmetering of the catalyst in the compositions. The mechanical properties, such as the through-cure rate, the breaking stress, the elongation at break or the tensile shear strength, for example, are very largely independent over a wide range of catalyst concentration in the composition as a whole. For example, S2 dumbbell specimens feature a maximum relative variance in breaking stress of only 25%. The variance is calculated by forming differences from the values, and is based on the highest value in each case. Furthermore, adhesive bonds exhibit a maximum variance in tensile shear strength of only up to 20% or less.

By contrast, products produced with assistance from tin catalysts, for example, generally have large variances. Thus, when the amount of catalyst is doubled, the tensile shear strength drops by more than 25%, preferably more than 30%. In particular, when the amount of catalyst is increased from about 0.5 wt % to about 1 wt %, based on the mass of the overall composition, the tensile shear strength drops by more than 40%.

Furthermore, the special product safety of the inventive use is characterized by an improved toxicological profile of the catalysts by comparison with a large number of heavy metal-containing catalyst systems known from the prior art, including organotin-containing or organobismuth-containing catalyst systems, more particularly organotin-containing catalyst systems.

The method of the invention for the curing of compounds containing alkoxysilyl groups, to form Si—O—Si bonds, by means of at least one compound of the invention having guanidine groups and containing semi-organic silicon groups as curing catalyst, is carried out preferably at room temperature.

A preferred method of the invention is that in which the compounds containing alkoxysilyl groups are cured without addition of metal compounds.

Preferred metal catalysts are tin compounds such as, for example, tin diacetate, tin dioctoate, dibutyltin diacetylacetonate, dibutyltin dilaurate, tin tetraacetate, dibutyltin diacetate, dibutyltin dioctoate, dibutyltin dilaurate, dibutyltin dioleate, dimethoxydibutyltin, dimethyltin, dibutyltin benzylmaleate, bis(triethoxysiloxy)dibutyltin, diphenyltin diacetate, and bismuth compounds, such as bismuth carboxylates, for example, and also titanium compounds, such as tetraethoxytitanium, tetra-n-propoxytitanium, tetraisopropoxytitanium, tetra-n-butoxytitanium, tetraisobutoxy-titanium, tetrakis(2-ethylhexoxy)titanium, diisopropoxybis(ethylacetoacetato)titanium, dipropoxybis(acetylacetonate)titanium, diisopropoxybis(acetylacetonato)titanium, dibutoxybis(acetylacetonato)titanium, triisopropoxyallyltitanium acetate, iso-propoxyoctylene glycol or bis(acetylacetonato) titanium oxide, and lead compounds, such as lead diacetate, lead di-2-ethylhexanoate, lead dineodecanoate, lead tetraacetate, lead tetrapropionate, for example, and zinc compounds, such as zinc acetylacetonate, zinc 2-ethylcaproate, zinc diacetate, bis(2-ethylhexanoyl)zinc, zinc dineodecanoate, zinc diundecenoate, zinc dimethacrylate, for example, and also zirconium compounds, such as, for example, tetrakis(2-ethylhexanoyl)zirconium dichloride, tetrakis(methacryloyl)zirconium dichloride, and cobalt diacetate. Furthermore, use may also be made of bismuth catalysts, and also iron(II) and iron(III) compounds, e.g. iron(III) acetylacetonate or iron diacetate, and also aluminium compounds, e.g. aluminium acetylacetonate, and calcium compounds, e.g. calcium ethylenediaminetetraacetate, and also magnesium compounds, e.g. magnesium ethylenediaminetetraacetate.

Especially preferred are the methods in which the compounds containing alkoxysilyl groups are cured without addition of tin compounds and/or bismuth compounds.

Preferred compounds containing alkoxysilyl groups that can be cured with the method of the invention have been described above.

The products of the method of the invention have the abovementioned advantages in relation to mismetering of the catalyst. More particularly, the products according to the method have the mechanical advantages stated above.

Furthermore, the easy handling of the liquid and storage-stable catalysts has proved to be a further advantage relative to conventional metal catalysts which are unstable towards hydrolysis. The stability towards hydrolysis should be emphasized particularly here, since catalysts such as titanates or zirconates, for example, are deactivated by hydrolysis and subsequent self-condensation. The catalysts of the invention do not have this defect; they suffer no loss in activity.

The compounds of the invention having guanidine groups and containing semi-organic silicon groups, the compositions of the invention comprising at least one compound having guanidine groups and containing semi-organic silicon groups, and also the inventive use of the compounds having guanidine groups and containing semi-organic silicon groups, and of their compositions, and additionally the method of the invention using the compounds of the invention having guanidine groups and containing semi-organic silicon groups, are described by way of example below, without any intention that the invention should be confined to these exemplary embodiments. References below to ranges, general formulae or classes of compound should be taken to encompass not only the corresponding ranges or groups of compounds that are explicitly mentioned, but also all sub-ranges and sub-groups of compounds that may be obtained by extracting individual values (ranges) or compounds. Where documents are cited in the context of the present description, it is intended that their content fully form part of the disclosure content of the present invention. Where % figures are given below, they are figures in weight % unless otherwise indicated. In the case of compositions, the % figures, unless otherwise indicated, are based on the overall composition. Where average values are reported below, the averages in question are mass averages (weight averages), unless otherwise indicated. Where measurement values are reported below, these measurement values, unless otherwise indicated, have been ascertained under a pressure of 101325 Pa and at a temperature at 25° C.

OPERATIVE EXAMPLES

The subject matter of the present invention is elucidated in more detail below, without any intention that the subject matter of the invention should be confined to these exemplary embodiments.

| General Methods and Materials | | |
|---|---|---|
| Diisononyl phthalate | Vestinol 9 (DINP) | Evonik Industries AG, Essen |
| Diisoundecyl phthalate | DIUP | Evonik Industries AG, Essen |
| Precipitated calcium carbonate | Socal U1S2 | Solvay Chemicals GmbH, Rheinberg |
| Titanium dioxide | Kronos 2310 | Kronos Titan GmbH, Leverkusen |
| Aerosil R202 | | Evonik Industries AG, Essen |
| Aerosil R974 | | Evonik Industries AG, Essen |
| Irganox 1135 | | BASF, Ludwigshafen |
| Tinuvin 292 | | BASF, Ludwigshafen |
| Tinuvin 1130 | | BASF, Ludwigshafen |
| Butyl titanate | TYZOR ® TBT | Du Pont Europe, Belgium |
| Karstedt catalyst preparation, 1% Pt° in decamethylcyclopentasiloxane | | Evonik Industries AG, Essen |
| Dioctyltin diketonate | TIB KAT ® 223 | TIB Chemicals, Mannheim |
| Polypropylene oxide | PPG (2000 g/mol) | BayerMaterial Science, Leverkusen |
| Isophorone diisocyanate | IPDI | Evonik Industries AG, Essen |
| Hexamethyldisiloxane, 98% | Cat. No. AB111176 | ABCR, Karlsruhe |
| Decamethylcyclopentasiloxane, 97% | Cat. No. AB111012 | ABCR, Karlsruhe |
| Phenylmethylcyclosiloxane, 95% | Cat. No. AB153228 | ABCR, Karlsruhe |
| Bis(aminopropyl)tetramethyldisiloxane, 97% | Cat. No. AB110832 | ABCR, Karlsruhe |
| Trifluoromethanesulphonic acid, >99% | Cat. No. 347817 | Sigma-Aldrich Chemie GmbH, Munich |
| 1,1,3,3-Tetramethylguanidine (TMG), 99% | Cat. No. 241768 | Sigma-Aldrich Chemie GmbH, Munich |
| N,N-Dicyclohexylcarbodiimide (DCC), 99% | Cat. No. D80002 | Sigma-Aldrich Chemie GmbH, Munich |
| Tetramethylammonium hydroxide*5$H_2O$, >97% | Cat. No. T7505 | Sigma-Aldrich Chemie GmbH, Munich |
| Lewatit ® K 2621 | | LANXESS Deutschland GmbH, Leverkusen |
| 3-Glycidyloxypropyltriethoxysilane | Dynasylan GLYEO | Evonik Industries AG, Essen |
| Dynasylan ® 1505 | | Evonik Industries, Essen |
| Dynasylan 1146 | | Evonik Industries AG, Essen |
| Dynasylan VTMO | | Evonik Industries AG, Essen |
| Dynasylan AMMO | | Evonik Industries AG, Essen |

Viscosity:

The viscosities were determined, if indicated, by means of a Brookfield LV-DV-I+ spindle viscometer. Brookfield viscometers are rotary viscometers having defined spindle sets as rotary bodies. The rotary bodies used were from an LV spindle set. Owing to the temperature dependence of viscosity, the temperatures of the viscometer and of the measuring liquid were kept constant during the measurement, with an accuracy of +/−0.5° C. Further materials used in addition to the LV spindle set were a thermostatable waterbath, a 0-100° C. thermometer (scale divisions 1° C. or smaller) and a timer (scale values not greater than 0.1 second). To perform the measurement, 100 ml of the sample were introduced into a wide-necked bottle and measured under temperature-controlled conditions in the absence of air bubbles after prior calibration. To determine the viscosity, the viscometer was positioned relative to the sample such that the spindle dips into the product up to the mark. The measurement is initiated by activation of the start button, while care was taken to ensure that the measurement took place in the most favourable region of 50% (+/−20%) of the maximum measurable torque. The result of the measurement was displayed by the viscometer in mPas, while division by the density (g/ml) gives the viscosity in $mm^2/s$.

Spectroscopic Analyses:

The recording and interpretation of NMR spectra is known to the skilled person. References include the book "NMR Spectra of Polymers and Polymer Additives", A. Brandolini and D. Hills, 2000, Marcel Dekker, Inc. The spectra were recorded at room temperature with a Bruker Spectrospin spectrometer, with measurement frequencies when recording the proton spectra of 399.9 MHz, when recording the $^{13}C$ spectra of 100.6 MHz and when recording the $^{29}Si$ spectra of 79.5 MHz. In view of the basicity of the guanidinosiloxanes prepared, the use of chlorine-containing deuterated solvents was abandoned, and instead acetone-d6 or methanol-d4 (Sigma-Aldrich) was used. The guanidines were identified by monitoring the formation of product in the $^{13}C$ NMR. Thus, for example, the signal of the carbodiimide carbon (RN=C=NR) is a $\delta$=140 ppm, and the signal of the guanidine group, depending on the substitution pattern of the guanidine HRN—C(=NR)—NRH, is at $\delta$=150-160 ppm. Reference may be made again at this point to the publication by Xuehua Zhu, Zhu Du, Fan Xu and Qi Shen (J. Org. Chem. 2009, 74, 6347-6349) and to the textbooks by Frederick Kurzer, K. Douragh-Zader—"Advances in the Chemistry of Carbodiimides" (Chemical Reviews, Vol. 67, No. 2, 1967, p. 99 ff.) and Henri Ulrich—"Chemistry and Technology of Carbodiimides" (John Wiley & Sons Ltd., ISBN 978-0-470-06510-5, 2007).

Determination of Total Nitrogen Content:

Basic nitrogen is determined by potentiometric titration with perchloric acid in a non-aqueous medium.

Determination of Relative Molar Mass of a Polymer Sample by Gel Permeation Chromatography (GPC):

The gel permeation chromatography analyses (GPC) took place with a Hewlett-Packard 1100 instrument, using an SDV column combination (1000/10 000 Å, each 65 cm, internal diameter 0.8 cm, temperature 30° C.), THF as mobile phase with a flow rate of 1 ml/min and with an RI detector (Hewlett-Packard). The system was calibrated against a polystyrene standard in the 162-2 520 000 g/mol range.

Inert Method:

Under "inert" conditions is meant that the gas space within the apparatus is filled with an inert gas, e.g. nitrogen or argon. This is achieved by the flooding of the apparatus, with continuing inertization being ensured by the application of a permanent gentle stream of inert gas.

Example 1

Synthesis Examples

S1 (E6): Preparation of an Aminopropylmethyldimethoxysilane Condensate

A 250 ml four-necked flask equipped with KPG stirrer, reflux condenser, nitrogen inlet, temperature sensor and heating hood was charged under inert conditions with 100 g (520 mmol) of aminopropylmethyldiethoxysilane (Dynasilan® 1505) and this initial charge was heated to 80° C. Then 18.8 g (1.04 mol) of DI water were added in portions and the mixture was maintained at 75-85° C. for two hours. After the end of hydrolysis, concentration took place on a rotary evaporator at 80° C. and 10-25 mbar. This gave a clear product, with a viscosity much higher than that of the reactant, of the general formula HO—[Si$^{(CH2)3NH2}$Me]$_n$-OH with n=11-16.

S2 (E1): Preparation of a Linear Aminosiloxane by Equilibration of a Condensate Prepared According to S1 with HMDS A 250 ml four-necked flask equipped with KPG stirrer, reflux condenser, nitrogen inlet, temperature sensor and heating hood was charged under inert conditions with 75.08 g of a condensate according to S1 having a nitrogen value of $N_{tot.}$=11.5 wt % and a viscosity of 807 mPas (Brookfield), and 74.9 g of hexamethyldisiloxane were added. While the reaction mixture was stirred, then 0.08 g (=0.05 wt %) of tetramethylammonium hydroxide was added, and heating took place to 90° C. The two-phase reaction mixture, which was turbid and colourless, became homogeneous and clear after a reaction time of 1 hour, but turned slightly turbid again over the total reaction time of 6.5 hours. After the end of the reaction time, the catalyst was destroyed on a rotary evaporator at 150° C. and 1 mbar for 3 hours. A fraction of volatile constituents of 31.8 wt % was ascertained. The $^{29}Si$ NMR analysis of the end product confirmed the structure of M-[D$^{(CH2)3NH2}$]$_{3.3}$-M, and a nitrogen value of $N_{tot}$=8.5 wt % was found.

S3 (H1): Hydrosilylation of Allyl Glycidyl Ether with a Comb like Hydrogensiloxane A 1000 ml multi-necked flask equipped with KPG stirrer, reflux condenser, nitrogen inlet, temperature sensor, dropping funnel and heating hood was charged under inert conditions with 95.4 g (0.84 mol) of allyl glycidyl ether, and this initial charge was heated to 70° C. Subsequently, in a counter-current stream of nitrogen, 198 mg of a Karstedt catalyst preparation (corresponding to 5 ppm of Pt$^0$) were added. Then, over the course of 30 minutes, 300 g of a pendant hydrogensiloxane (2.23 mol SiH/kg) were added from a dropping funnel. The dropping speed was regulated so that a reaction temperature of not more than 90° C. was attained. After 3 hours, the SiH conversion was found by gas volumetry to be 82%. To complete the reaction, a further 20 g (0.18 mol) of allyl glycidyl ether and 99 mg of the Karstedt catalyst preparation (corresponding to 2.5 ppm of Pt$^0$) were added, and the reaction was thus taken to an SiH conversion >99% at 70° C. within a further 7 hours. The product obtained was distilled on a rotary evaporator at 130° C. and a pressure <1 mbar for a number of hours. This gave the epoxy-functional siloxane as a clear, pale yellowish liquid. Investigation by means of $^{29}Si$ NMR confirmed the target structure.

S4 (N1): Ring Opening of Epoxide S3 with Ammonia

The resulting product S3 was subjected in analogy to WO 2011095261 (US 2012/282210) to an epoxidic ring opening by means of ammonia. This was done by taking up 50 g of the epoxysiloxane into 100 g of isopropanol and transferring the mixture to an autoclave tube. Using a mixture of ethanol and dry ice, the outer wall of the autoclave tube was cooled down such that 10.9 g of ammonia were condensed in by simple introduction using a glass frit over 30 minutes. The tube was closed and heated at 100° C. for 4 hours. The isopropanol and excess ammonia were then distilled off on a rotary evaporator within an hour at 60° C. and <1 mbar. Wet-chemical determination of the primary nitrogen value gave 2.8 wt %, in agreement with the theoretical value.

S5 (G1): Preparation of a Guanidine by Reaction of Synthesis Product S4

A 250 ml four-necked flask equipped with KPG stirrer, distillation bridge with vacuum attachment, nitrogen blanketing, temperature sensor and heating hood was charged under inert conditions with 71.13 g (147.34 mmol/-NH2) of the amino-functional siloxane from the preceding stage and with 28.87 g (139.92 mmol) of N,N-dicyclohexylcarbodiimide, and these components were reacted with one another at 90° C. for 10 hours. After the end of the reaction time, all of the volatile constituents were distilled off within an hour at 90° C. and 20 mbar under a diaphragm pump vacuum. Investigation by $^{29}$Si and $^{13}$C NMR confirmed the target structure of the clear, pale yellowish product.

S6 (H2): Hydrosilylation of Allyl Glycidyl Ether with a Cyclic Hydrogensiloxane

A 1000 ml multi-necked flask equipped with KPG stirrer, reflux condenser, nitrogen inlet, temperature sensor, dropping funnel and heating hood was charged under inert conditions with 93.3 g (0.82 mol) of allyl glycidyl ether, and this initial charge was heated to 70° C. Subsequently, in a countercurrent stream of nitrogen, 197 mg of a Karstedt catalyst preparation (corresponding to 5 ppm of Pt$^0$) were added. Then, over the course of 30 minutes, 300 g of a cyclic hydrogensiloxane (2.18 mol SiH/kg) were added from a dropping funnel. The dropping speed was regulated so that a reaction temperature of not more than 90° C. was attained. After 3.5 hours, the SiH conversion was found by gas volumetry to be 74%. To complete the reaction, a further 19 g (0.17 mol) of allyl glycidyl ether and 197 mg of the Karstedt catalyst preparation (corresponding to 5 ppm of Pt$^0$) were added, and the reaction was thus taken to an SiH conversion >99% at 70° C. within a further 7 hours. The product obtained was distilled on a rotary evaporator at 100° C. and a pressure of 15 mbar for a number of hours. This gave the epoxy-functional siloxane as a clear, pale yellowish liquid. Investigation by means of $^{29}$Si NMR confirmed the target structure, with a theoretical epoxy value of 2.79%.

S7 (N2): Ring Opening of Epoxide S6 with Ammonia

The resulting product (S6) was further subjected in analogy to WO 2011095261 (US 2012/282210) to an epoxidic ring opening by means of ammonia. For this purpose, 250 g of the epoxysiloxane (theoretical epoxy value 2.79%) were taken up in 500 g of isopropanol, and transferred to an autoclave tube. Using a mixture of ethanol and dry ice, the outer wall of the autoclave tube was cooled down such that 60 g of ammonia (710% excess) were condensed in by simple introduction using a glass frit over 30 minutes. The tube was closed and heated at 100° C. for 4 hours, during which a pressure increase to 22 bar was recorded. After the end of the reaction time, the mixture was cooled to room temperature and the pressure vessel was let down. The isopropanol and excess ammonia were then distilled off on a rotary evaporator within an hour at 60° C. and <1 mbar. Wet-chemical determination of the primary nitrogen value gave 2.8 wt %, in agreement with the theoretical value.

S8 (G2): Preparation of a Cyclic Siloxane Having Guanidine Groups

A 250 ml four-necked flask equipped with KPG stirrer, distillation bridge with vacuum attachment, nitrogen blanketing, temperature sensor and heating hood was charged under inert conditions with 75.72 g (156.84 mmol/-NH2) of the amino-functional siloxane from the preceding stage S7 and with 24.28 g (117.67 mmol) of N,N-dicyclohexylcarbodiimide, and these components were reacted at 90° C. for 10 hours. After the end of the reaction time, all of the volatile constituents were distilled off within an hour at 90° C. and 20 mbar under a diaphragm pump vacuum. Investigation by $^{29}$Si and $^{13}$C NMR confirmed the target structure of the clear, pale orange-coloured product.

S9 (E3): Equilibration of the Condensate S1 to Form a Cyclic Aminopropylsiloxane A 1000 ml multi-necked flask equipped with KPG stirrer, reflux condenser, nitrogen inlet, temperature sensor, dropping funnel and heating hood was charged under inert conditions with 61.2 g (522 mmol/-NH2) of a condensate prepared according to S1, and 38.8 g (523 mmol/D) of octamethylcyclotetrasiloxane, 400 g of xylene and 2.5 g of tetramethylammonium hydroxide * pentahydrate (TMAH*5H$_2$O) were added. The reaction mixture was heated at 90° C. for 6 hours and then heated at reflux for 8 hours to destroy the catalyst. The continuous reduction in amine level during this procedure was measured using a pH paper in a stream of nitrogen. When destruction of the catalyst was at an end, the solvent was removed on a rotary evaporator and intensive distillation took place on the rotary evaporator at 100° C. and <1 mbar for 1 hour. The slightly turbid product, finally, was filtered through a fluted filter, giving a clear and colourless product.

S10 (G3): Preparation of a Cyclic Guanidine by Reaction of a Cyclic Aminosiloxane with DCC A 250 ml multi-necked flask equipped with KPG stirrer, reflux condenser, nitrogen inlet, temperature sensor and heating hood was charged under inert conditions with 80 g of the cyclic aminopropylsiloxane S9 and admixed with 82.6 g (400 mmol) of N,N-dicyclohexylcarbodiimide (DCC). The mixture was reacted at 90° C. for six hours, after which volatile constituents were removed by distillation under 15 mbar for an hour. The product was obtained as a clear, slightly yellowish product, which was solid at room temperature. Analysis by means of $^{13}$C NMR spectroscopy showed the complete conversion of the carbodiimide.

S11 (E4): Equilibration of the Condensate S1 to Form a Cyclic Aminopropylphenylmethylsiloxane A 250 ml multi-necked flask equipped with KPG stirrer, reflux condenser, nitrogen inlet, temperature sensor, dropping funnel and heating hood was charged under inert conditions with 11.6 g (99 mmol/-NH2) of a condensate prepared according to S1, and 13.5 g (99 mmol/D$^{PhMe}$) of phenylmethylcyclotetrasiloxane (CAS 546-45-2), 100 g of xylene and 0.6 g of tetramethylammoniumhydroxide pentahydrate (TMAH*5H$_2$O) were added. The reaction mixture was heated at 90° C. for 6 hours and then heated at reflux for 8 hours to destroy the catalyst. The continuous reduction in amine level during this procedure was measured using a pH paper in a stream of nitrogen. When destruction of the catalyst was at an end, the solvent was removed on a rotary evaporator and intensive distillation took place on the rotary evaporator at 100° C. and <1 mbar for one hour. The slightly turbid product, finally, was filtered through a fluted filter, giving a clear and colourless product.

S12 (G4): Preparation of a Cyclic Siloxane Containing Guanidine Groups by Reaction of a Cyclic Aminopropylphenylmethylsiloxane with DCC A 100 ml multi-necked flask equipped with KPG stirrer, reflux condenser, nitrogen inlet, temperature sensor and heating hood was charged under inert conditions with 21.4 g (84.5 mmol/-NH$_2$) of the cyclic aminopropylphenylmethylsiloxane (S11) and admixed with 16.6 g (80.5 mmol) of N,N-dicyclohexylcarbodiimide (DCC). The mixture was reacted at 90° C. for six hours, after which volatile constituents were removed by distillation under 15 mbar for an hour. The product was obtained as a clear, slightly yellowish product, which was solid at room temperature. Analysis by means of $^{13}$C NMR spectroscopy showed the complete conversion of the carbodiimide.

S13 (G5): Synthesis of a Cyclotetrasiloxane Containing Guanidino Groups by Reaction of tetra(chloropropyl)tetramethylcyclosiloxane with Tetramethylguanidine A 500 ml multi-necked flask equipped with KPG stirrer, reflux condenser, nitrogen inlet, temperature sensor and heating hood was charged under inert conditions with 50 g (0.37 mol) of tetra(chloropropyl)tetramethylcyclosiloxane D$_4^{(CH2)3Cl}$, which was obtained by preceding aqueous hydrolysis/condensation of a chloropropyldichloromethylsilane, and this initial charge was heated to 60° C., and a quantity of 126.4 g (1.1 mol) of tetramethylguanidine was added over 30 minutes. The reaction temperature was raised to 130° C. and maintained for 6 hours; as the reaction time progressed, copious formation of salt was observed. After the end of the reaction time, the product was left to cool to room temperature and was diluted with 100 ml of toluene. The product was then freed from the salt on a filter press (Seitz K300), after which it was freed from unreacted tetramethylguanidine on a rotary evaporator at 100° C. under a pressure <1 mbar for 1 hour. Distillation gave the cyclic tetraguanidinopropyltetrasiloxane as a turbid, slightly yellowish product. Analysis by $^1$H and $^{29}$Si NMR confirmed the structure.

S14 (G6): Synthesis of a Cyclic Guanidinosiloxane by Reaction of 2,4,6,8-tetrakis(3-chloropropyl)-2,4,6,8-tetramethylcyclotetrasiloxane [D$_4^{(C3H6Cl)}$] with TMG A 500 ml multi-necked flask equipped with KPG stirrer, dropping funnel, internal temperature measurement sensor and inert gas feed line was copiously inertized with nitrogen and then charged with 100 g (183 mmol=732 mmol/-C$_3$H$_6$Cl) of 2,4,6,8-tetrakis(3-chloropropyl)-2,4,6,8-tetramethylcyclotetrasiloxane [CAS 96322-87-1], which was heated to 60° C. Then 252.8 g (2.2 mol) of tetramethylguanidine were metered in, and the mixture was heated at 130° C. for 6 hours. After the onset of copious precipitation of salt, 200 ml of toluene were added in order to keep the batch stirrable. After the end of the reaction, the salt was separated using a filter press over a Seitz K300 filter. Unreacted tetramethylguanidine was removed subsequently from the filtrate by distillation under a severe oil pump vacuum (<1 mbar) at 100° C. for 1 hour. The viscous, slightly yellowish and turbid product obtained was discharged under inert gas.

S15 (E5): Equilibration of Phenylmethylcyclosiloxane and 2,4,6,8-tetrakis(3-chloropropyl)-2,4,6,8-tetramethylcyclotetrasiloxane A 250 ml multi-necked flask equipped with KPG stirrer, dropping funnel, internal temperature measurement sensor and inert gas feed line was copiously inertized with nitrogen and then charged with 20 g (147 mmol) of phenylmethylcyclosiloxane (CAS 546-45-2). Then 20 g (36.6 mmol=147 mmol/-C$_3$H$_6$Cl) of tetrakis(3-chloropropyl)-2,4,6,8-tetramethylcyclotetrasiloxane, 160 g of toluene and 12 g of Lewatit® K2621 were added. Equilibration was then carried out at 60° C. for 6 hours, and the Lewatit® catalyst was separated off on a fluted filter. The filtrate was freed from toluene on a rotary evaporator, and then distilled fully at 70° C. and <1 mbar for an hour. The clear, colourless product thus obtained was discharged under inert gas.

S16 (G7): Synthesis of a Cyclic Guanidinosiloxane by Reaction of S15 with Tetramethylguanidine A 500 ml multi-necked flask equipped with KPG stirrer, dropping funnel, internal temperature measurement sensor and inert gas feed line was inertized copiously with nitrogen and then charged with 30 g (55 mmol=110 mmol/-C$_3$H$_6$Cl) of S15 equilibrate, and 38 g (330 mmol) of tetramethylguanidine and 40 g of xylene were added. The reaction mixture was heated and held at a reaction temperature of 130° C. for 6 hours. After the end of reaction, a Seitz K300 filter in a filter press was used to separate off the precipitated tetramethyl hydrochloride. Unreacted tetramethylguanidine and the solvent were subsequently removed from the filtrate by distillation under an intense oil pump vacuum (<1 mbar) at 100° C. for an hour. The highly viscous, slightly yellowish and clear product obtained was discharged under inert gas.

S17 (G8): Synthesis of 2',2'-((1,1,3,3-tetramethyldisiloxane-1,3-diyl)bis(propane-3,1-diyl))bis(1,3-dicyclohexylguanidine)

A 250 ml four-necked flask equipped with KPG stirrer, reflux condenser, nitrogen blanketing, temperature sensor and heating hood was charged under inert conditions with 24.85 g (100 mmol) of 1,3-bis(3-aminopropyl)tetramethyldisiloxane, and 40.44 g (196 mmol) of N,N-dicyclohexylcarbodiimide were added. With continuing stirring, the reaction mixture was reacted at 90° C. for 6 hours, after which all of the volatile constituents were distilled off over 30 minutes under a diaphragm pump vacuum. This gave a clear, viscous product, which after analysis by means of $^{13}$C NMR showed complete conversion of the carbodiimide.

S18 (G9): Reaction of the Condensate S1 with DCC

A 500 ml four-necked flask equipped with KPG stirrer, reflux condenser, nitrogen blanketing, temperature sensor and heating hood was charged under inert conditions with 128.09 g of a condensate as per S1 (N value=11.3 wt %, 122.5 g/eq —NH$_2$, =1.05 mol —NH2), and 71.91 g (348.52 mmol) of N,N-dicyclohexylcarbodiimide were added. With continuous stirring, the reaction mixture was reacted at 90° C. for 6 hours, after which all of the volatile constituents were distilled off over 30 minutes under a diaphragm pump vacuum. This gave a clear, viscous product (S18) which after analysis by means of $^{13}$C NMR showed complete conversion of the carbodiimide.

S19 (G10): Reaction of the Condensate S1 with DCC

A 500 ml four-necked flask equipped with KPG stirrer, reflux condenser, nitrogen blanketing, temperature sensor and heating hood was charged under inert conditions with 94.21 g of a condensate according to S1 (N value=11.3 wt %, 122.5 g/eq —NH$_2$, =769.1 mmol) and 105.79 g (512.72 mmol) of N,N-dicyclohexylcarbodiimide were added. With continuing stirring, the reaction mixture was reacted at 90° C. for 6 hours, after which all of the volatile constituents were distilled off over 30 minutes under a diaphragm pump vacuum. This gave a clear product, highly viscous in the hot state, which after analysis by means of $^{13}$C NMR showed complete conversion of the carbodiimide. After cooling to RT, the product solidified to form a clear mass, which was reversibly meltable, however.

S20 (E7): Preparation of a Linear Siloxane of the Formula MD$_3$D$^{C3H6Cl}$M

A 250 ml single-necked flask was charged with 39.3 g (288 mmol/D$^{C3H6Cl}$) of a chloropropyldichloromethylsilane hydrolysis condensate, 64 g (863 mmol/D) of decamethylcyclopentasiloxane and 46.7 g (288 mmol/MM) of hexamethyldisiloxane. With magnetic stirring, 0.15 g of trifluoromethanesulphonic acid was added and the batch was stirred overnight. The next day, the equilibration was completed on a rotary evaporator at 90° C. for 4 hours, after which the acid was deactivated by addition of 8 g of sodium hydrogencarbonate. Filtration on a fluted filter gave 158 g of a clear, colourless liquid. Analysis by $^{29}$Si NMR spectroscopy confirmed the structure [MD$_3$D$^{C3H6Cl}$M].

S21 (G11): Preparation of a Linear Siloxane Containing Guanidinopropyl Groups

A 250 ml four-necked flask equipped with KPG stirrer, reflux condenser, nitrogen inlet, temperature sensor and heating hood was charged under inert conditions with 80 g (153 mmol/D$^{C3H6Cl}$) of S20, and this initial charge was heated to 100° C. Then 53 g (460 mmol) of tetramethylguanidine were metered in via a dropping funnel over an hour, and the mixture was held at 130° C. for a further 8 hours. After the end of the reaction, the precipitated tetramethylguanidine hydrochloride was filtered off and the product was distilled under an oil pump vacuum at 6 mbar and 130° C. for an hour. A further filtration gave 55 g of a clear product. $^{29}$Si and $^{13}$C NMR analyses confirmed the structure.

S22 (E8): Preparation of a Linear Siloxane of the Formula MD$_3$D$^{C3H6NH2}$M

A 250 ml multi-necked flask equipped with KPG stirrer, reflux condenser, nitrogen inlet, temperature sensor, dropping funnel and heating hood was charged under inert conditions with 35 g (300 mmol/-NH2) of a condensate as per S1 with a nitrogen value of N$_{tot.}$=11.5 wt % and a viscosity of 807 mPas (Brookfield), and 66.58 g (900 mmol/D) of octamethylcyclotetrasiloxane, 48.5 g (300 mmol/MM) of hexamethyldisiloxane and 60 mg of tetramethylammonium hydroxide * pentahydrate (TMAH*5H$_2$O) were added. The reaction mixture was heated at 90° C. for 6 hours and then heated on a rotary evaporator at 130° C. for 3 hours in order to destroy the catalyst. When destruction of the catalyst was at an end, the solvent was removed on a rotary evaporator and subjected to intensive distillation on the rotary evaporator at 100° C. and <1 mbar for 1 hour. Lastly, the slightly turbid product was filtered through a fluted filter, to give a clear, colourless product which according to $^{29}$Si NMR had an approximate structure of M(DD$^{C3H6NH2}$)$_{7.4}$M.

S23 (G12): Preparation of a Linear Siloxane, Carrying Guanidine Groups, of the Formula MD$_3$D$^{C3H6-GUA}$M A 100 ml four-necked flask equipped with KPG stirrer, reflux condenser, nitrogen inlet, temperature sensor and heating hood was charged under inert conditions with 50 g (135 mmol/-NH$_2$) of the linear aminosiloxane prepared above (S22) (N$_{theor.}$=3.787%) and this initial charge was admixed with 26.5 g (128 mmol) of N,N-dicyclohexylcarbodiimide. The resulting reaction mixture was reacted at 90° C. for 6 hours, giving a colourless, slightly turbid product. Analysis by $^{13}$C NMR spectroscopy showed complete conversion of the carbodiimide. Subsequently, $^{29}$Si NMR spectroscopy found a siloxane chain length of N=5.6, indicating a structure of M(DD$^{C3H6GUA}$)$_{3.6}$M.

S24 (E9): Preparation of a Linear Aminopropylsiloxane by Equilibration of 51 with HMDS A 250 ml four-necked flask equipped with KPG stirrer, reflux condenser, nitrogen inlet, temperature sensor and heating hood was charged under inert conditions with 90 g of a condensate according to 51 with a nitrogen value of N$_{tot.}$=11.5 wt % and a viscosity of 807 mPas (Brookfield), and 60 g of hexamethyldisiloxane were added. Whilst stirring, the reaction mixture was then admixed with 0.08 g (=0.05 wt %) of tetramethylammonium hydroxide and heated to 90° C. After a reaction time of 1 hour, the two-phase reaction mixture, which was turbid and colourless, became homogeneous and clear. The catalyst was destroyed after the end of the reaction time, on a rotary evaporator at 150° C. and 1 mbar for 3 hours. The fraction of volatile constituents was found to be 20 wt %. The $^{29}$Si NMR analysis of the end product confirmed the structure of M-[D$^{(CH2)3NH2}$]$_{3.5}$-M, and a nitrogen value of N$_{tot}$=8.7 wt % was found.

S25 (G14): Preparation of a Linear Siloxane Containing Guanidinopropyl Groups

A 250 ml four-necked flask equipped with KPG stirrer, reflux condenser, nitrogen inlet, temperature sensor and heating hood was charged under inert conditions with 104.05 g (646 mmol/-NH$_2$) of the above S24-prepared linear aminosiloxane (N$_{theor.}$=8.7%), and 126.8 g (614 mmol) of N,N-dicyclohexylcarbodiimide were added. The resulting reaction mixture was reacted at 90° C. for 6 hours, giving a slightly yellowish product, colourless in the hot state, which became solid on cooling, but was reversibly meltable. Analysis by $^{13}$C NMR spectroscopy showed complete conversion of the carbodiimide. Moreover, $^{29}$Si NMR spectroscopy found a siloxane chain length of N=5.5, suggesting a structure of M(D$^{C3H6GUA}$)$_{3.5}$M.

S26 (G14): Preparation of a Linear Siloxane Containing Guanidinopropyl and Aminopropyl Groups A 100 ml four-necked flask equipped with KPG stirrer, reflux condenser, nitrogen inlet, temperature sensor and heating hood was charged under inert conditions with 49.18 g (299 mmol/-NH$_2$) of a linear aminosiloxane in analogy to S24 with a nitrogen value of N$_{theor.}$=8.5 wt %, and 30.8 g (149 mmol) of N,N-dicyclohexylcarbodiimide were added. The reaction mixture thus obtained was reacted at 90° C. for 6 hours, giving a colourless, clear product. Analysis by $^{13}$C NMR spectroscopy showed complete conversion of the carbodiimide. Moreover, $^{29}$Si NMR spectroscopy found a siloxane chain length of N=5.6, suggesting a structure of M(D$^{C3H6NH2}$)$_{-1.8}$(D$^{C3H6-GUA}$)$_{-1.8}$M.

S27 (G15): Preparation of a Linear Siloxane Containing Guanidinopropyl Groups

A 100 ml four-necked flask equipped with KPG stirrer, reflux condenser, nitrogen inlet, temperature sensor and heating hood was charged under inert conditions with 37.7 g (215 mmol/-NH$_2$) of a linear aminosiloxane prepared above in analogy to S24 (N=8.7 wt %), and 42.2 g (204 mmol) of N,N-dicyclohexylcarbodiimide were added. The reaction mixture thus obtained was reacted at 90° C. for 8 hours, giving a slightly yellowish, clear and viscous product. Analysis by $^{13}$C NMR spectroscopy showed complete conversion of the carbodiimide. Moreover, $^{29}$Si NMR spectroscopy found a siloxane chain length of N=4.7, suggesting a structure of M(DD$^{C3H6GUA}$)$^{2.7}$M.

S28: Preparation of a Linear, Hydroxyl-Terminated Siloxane Condensate Containing Guanidine Groups A 250 ml four-necked flask equipped with KPG stirrer, reflux condenser, nitrogen blanketing, temperature sensor and heating hood was charged under inert conditions with 102.08 g (232.24 mmol —NH2) of a linear siloxane condensate which has propyl groups and aminopropyl groups and is hydroxyl-terminated (N$_{prim.}$=3.64 wt %, M$_w$=~730 g/mol), and 47.92 g (232.24 mmol) of N,N-dicyclohexylcarbodiimide were added. With continuing stirring, the reaction mixture was reacted at 90° C. for 6 hours, after which all of the volatile constituents were distilled off over 30 minutes under a diaphragm pump vacuum. This gave a clear, viscous product, which according to analysis by $^{13}$C NMR showed complete conversion of the carbodiimide.

S29 (H3): Hydrosilylation of N-ethylmethallylamine (NE-MALA) Over a Cyclic Hydrogen Siloxane A 2000 ml multi-necked flask equipped with KPG stirrer, reflux condenser, nitrogen inlet, temperature sensor, dropping funnel and heating hood was charged under inert conditions with 756.3 g of a cyclic hydrogensiloxane (0.1332 wt %, corresponding to 756.3 g/eq SiH), 4.43 g of sodium carbonate were added, and the mixture was heated to a reaction temperature of 130° C. Shortly before reaction temperature was reached, 48 mg of di-p-chlorodichlorobis(cyclohexene)diplatinum(II) catalyst were added, and then in portions 885.25 g of N-ethylmethallylamine (NEMALA) were added via a dropping funnel in such a way that the reaction temperature did not exceed 145° C. The reaction was taken over seven hours at 130° C. to an SiH conversion >99%, with the reaction being monitored hourly by means of a determination by gas volumetry. The resulting reaction mixture was cooled to room temperature and filtered overnight, giving 881.50 g (theoretical 885.25 g). The subsequent multi-hour distillation under an oil pump vacuum at 130° C. and <1 mbar afforded 403.5 g (theoretical 406.24 g) of product, and 474 g (theoretical 478.96 g) of volatile compounds were condensed out under cooling with liquid nitrogen. The amino-functional cyclic siloxane was obtained as a clear, slightly yellowish liquid. Analysis by $^1H$, $^{13}C$ and $^{29}Si$ NMR confirmed the target structure.

S30 (G16): Preparation of a Guanidine by Reaction of the Synthesis Product S29

A 500 ml four-necked flask equipped with KPG stirrer, distillation bridge with vacuum attachment, nitrogen blanketing, temperature sensor and heating hood was charged under inert conditions with 203.12 g (500 mmol/-NH—) of the amino-functional siloxane from the preceding stage, S29, and with 59.95 g (475 mmol) of N,N-diisopropylcarbodiimide, and this mixture was reacted at 90° C. for 10 hours. After the end of the reaction time, all of the volatile constituents were distilled off over a further hour at 100° C. and 20 mbar under a diaphragm pump vacuum. Analysis by $^{29}Si$ and $^{13}C$ NMR confirmed the target structure of the clear, slightly yellowish product.

Example 2

Compositions/Formulations

In the compositions below, the quantity data in "parts" are based on parts by mass of any unit, and do not add up to 100.

Composition Z1:

25.9 parts of a polymer which carries alkoxysilyl groups were mixed with 18.1-18.6 parts of diisoundecyl phthalate, 50.5 parts of a precipitated chalk (Socal® U1S2, Solvay) and 0.5 part of the pigment titanium dioxide (Kronos® 2310, Kronos), and this mixture was homogenized by means of a Speedmixer (Speedmixer® FVS 600, Hausschild) (2300 rpm, 4 minutes). Thereafter the mixture was cooled to about 30° C. and 1.4 parts of adhesion promoter (Dynasylan® AMMO, Evonik), 1.1 parts of drying agent (Dynasylan® VTMO, Evonik), 1.5 parts of antioxidant/stabilizer mixture (ratio of Irganox® 1135:Tinuvin® 1130:Tinuvin® 292=1:2:2 ratio) and 0.5-2.0 parts of the curing catalyst were added. The mixture was again homogenized with a Speedmixer (2300 rpm, 1 minute).

Composition Z2:

25.9 parts of a polymer which carries alkoxysilyl groups were mixed with 20.1 parts of diisoundecyl phthalate, 50.5 parts of a precipitated chalk (Socal® U1S2, Solvay), and 0.5 part of titanium dioxide (Kronos® 2310, Kronos), and this mixture was homogenized by means of a Speedmixer (Speedmixer® FVS 600, Hausschild) (2300 rpm, 4 minutes). Thereafter the mixture was cooled to about 30° C. and 1.4 parts of adhesion promoter (Dynasylan® AMMO, Evonik), 1.1 parts of drying agent (Dynasylan® VTMO, Evonik) and 0.5 part of the curing catalyst were added. The mixture was again homogenized with a Speedmixer (2300 rpm, 1 minute).

Composition Z3:

25.9 parts of a polymer which carries alkoxysilyl groups were mixed with 17.1-18.1 parts of plasticizer (diisoundecyl phthalate) and 50.5 parts of a precipitated chalk as filler (Socal® U1S2, Solvay), and this mixture was homogenized by means of a Speedmixer (Speedmixer® FVS 600, Hausschild) (2300 rpm, 4 minutes). Thereafter the mixture was cooled to about 30° C. and 1.4 parts of adhesion promoter (Dynasylan® AMMO, Evonik), 1.1 parts of drying agent (Dynasylan® VTMO, Evonik), 1.5 parts of antioxidant/stabilizer mixture (ratio of Irganox® 1135:Tinuvin® 1130:Tinuvin® 292=1:2:2 ratio) and 0.5-2.0 parts of the curing catalyst were added. The mixture was again homogenized with a Speedmixer (2300 rpm, 1 minute).

Composition Z4:

36.1 parts of an alkoxylation product which carries alkoxysilyl groups were mixed with 11.0 parts of diisoundecyl phthalate, 44.8 parts of a precipitated chalk (Socal® U1S2, Solvay), 3.5 wt % of silica (Aerosil® R 974, Evonik) and 0.4 part of titanium dioxide (Kronos® 2310, Kronos), and this mixture was homogenized using a Speedmixer (Speedmixer® FVS 600, Hausschild) (2300 rpm, 4 minutes). Thereafter the mixture was cooled to about 30° C. and 1.7 parts of adhesion promoter (Dynasylan® 1146, Evonik), 1.5 parts of drying agent (Dynasylan® VTMO, Evonik), 0.5 part of Irganox® 1135 and 0.5 part of the curing catalyst were added. The mixture was again homogenized with a Speedmixer (2300 rpm, 1 minute).

Composition Z5:

36.8 parts of a polymer which carries alkoxysilyl groups were mixed with 44.2 parts of a precipitated chalk (Socal® U1S2, Solvay), 11 parts of a rheological additive (Vestinol 9 (DINP), Evonik), 0.4 part of titanium dioxide (Kronos® 2310, Kronos) and 3.5 parts of a rheological additive (Aerosil R202®), and this mixture was homogenized using a Speedmixer (Speedmixer® FVS 600, Hausschild) (2300 rpm, 4 minutes). Thereafter the mixture was cooled to about 30° C. and 1.0 part of drying agent (Dynasylan® VTMO, Evonik), 1.7 parts of adhesion promoter (Dynasylan® AMMO, Evonik), 0.5 part of stabilizer (Irganox® 1135, BASF) and 0.5-2.0 parts of the curing catalyst were added. The mixture was again homogenized with a Speedmixer (2300 rpm, 1 minute).

TABLE 1

Compositions (inventive Z1.1 to Z1.8, Z2.1), (non-inventive Z1.10, Z1.11) comprising a polyoxypropylene carrying alkoxysilyl groups pendantly (TP-2)

| Composition | Catalyst | Amount of cat. [parts] |
|---|---|---|
| Z1.1 | S25 | 1.0 |
| Z1.2 | S25 | 2.0 |
| Z1.3 | S26 | 1.0 |
| Z1.4 | S26 | 2.0 |
| Z1.5 | S27 | 1.0 |
| Z1.6 | S27 | 2.0 |
| Z1.7 | S17 | 0.5 |
| Z1.8 | S17 | 1.0 |
| Z2.1 | S17 | 0.5 |
| Z1.10 | TIB CAT 223 | 1.0 |
| Z1.11 | TIB CAT 223 | 0.5 |

TABLE 2

Compositions (inventive Z5.1, Z5.2, Z6.1), (non-inventive Z5.10, Z6.10) comprising a polyoxypropylene carrying alkoxysilyl groups pendantly (TP-1)

| Composition | Catalyst | Amount of cat. [parts] |
|---|---|---|
| Z1.12 | S18 | 1.0 |
| Z1.13 | S18 | 2.0 |
| Z5.1 | S18 | 1.0 |
| Z1.14 | TIB CAT 223 | 1.0 |
| Z5.10 | TIB CAT 223 | 1.0 |

TABLE 3

Compositions comprising different polymers carrying alkoxysilyl groups and the catalyst of Example 1 in an amount of one part (1 part) according to Example 2

| Composition | Polymer | Cat. |
|---|---|---|
| Z5.2 | TP-1 | S28 |
| Z5.3 | Polymer ST 61 | S28 |
| Z5.4 | Desmoseal S XP 26935 | S28 |

Example 3

Use

All of the completed formulations were transferred to PE cartridges and prior to application were stored at room temperature for at least 24 hours.

Determination of Breaking Stress and Elongation at Break:

The formulation was knifecoated in a film thickness of 2 mm on a PE surface. The films were stored for 7 days at 23° C. and 50% relative humidity. S2 dumbbell specimens were then punched from the films with the aid of a cutter and a toggle press. The dumbbell specimens thus produced were clamped for testing into a universal testing machine (from Shimadzu), and determinations were made of the breaking stress and elongation at break when the specimens were stretched at a constant velocity (200 mm/min). This determination was made in accordance with DIN 53504.

Determination of Tensile Shear Strength:

Overlap bonds were produced with the prepared formulation. For these bonds, two stainless steel substrates (V2A, 1.4301) were used. The region of the overlap bond amounted to 500 mm². The bonds were cured at 23° C. and 50% relative humidity. After 21 days, the bonds were clamped into a universal testing machine (from Shimadzu), and a force was exerted on the adhesive bond at a constant rate (10 mm/min) until the bond fractured. This determination was made in accordance with DIN EN 1465.

Determination of the Through-Cure Rate:

Method 1: A bead of adhesive or sealant was applied to a PE surface (height: 10 mm, width: 20 mm). After 24 hours of storage at 23° C. and 50% relative humidity, a section was cut from the bead, and the thickness of the cured film is measured using a caliper rule.

Method 2: The cure rate was determined by means of a wedge coater fabricated from a Teflon block. The wedge milled into the block is filled with the curable composition and smoothed off to the level of the block edges. This produces a distribution in film thickness over the length of the block of the curable composition of 0-10 mm. The filled wedge is stored at 23° C. and at 50% relative humidity. At the time of the determination of the cured film, the cured material is lifted, starting from the thin end of the wedge, and the thickness of the cured film is ascertained. A film is considered to be cured over the thickness thereof that possesses a direct mechanical cohesion with the cured surface, without still containing liquid or gelatinous fractions.

TABLE 4

Determination of the through-cure rate, breaking stress, elongation at break and tensile shear strength according to Example 3 of compositions according to Example 2 comprising different catalysts according to Table 1

| | Through-cure, method 1 after 24 h [mm] | Breaking stress [N/mm²] | Elongation at break [%] | Tensile shear strength [N/mm²] |
|---|---|---|---|---|
| Z1.1 | 2.6 | 1.3 | 250 | 0.53 |
| Z1.2 | 1.8 | 1.4 | 232 | 0.52 |
| Z1.3 | 2.4 | 0.9 | 305 | 0.50 |
| Z1.4 | 2.7 | 1.2 | 306 | 0.53 |
| Z1.5 | 2.6 | 1.3 | 255 | 0.46 |
| Z1.6 | 2.4 | 1.3 | 237 | 0.46 |
| Z1.7 | 2.0 | 1.4 | 293 | 0.90 |
| Z1.8 | 2.6 | 1.4 | 285 | 0.81 |
| Z2.1 | 2.0 | 2.0 | 250 | 1.08 |
| Z1.10 | 2.4 | 1.3 | 271 | 0.50 |
| Z1.11 | 2.4 | 1.6 | 262 | 0.86 |

The results shown in Table 4 show that good through-cure results and also good mechanical properties are achieved by the use of siloxanes containing guanidine groups in the adhesive and sealant formulations. The properties achieved are comparable with or better than those of the compositions comprising tin catalysts.

TABLE 5

Determination of the through-cure rate, breaking stress and elongation at break according to Example 3 of compositions according to Example 2 comprising the catalyst S18 at levels according to Table 2

| | Through-cure, method 2 after 5 days [mm] | Breaking stress [N/mm²] | Elongation at break [%] |
|---|---|---|---|
| Z1.12 | 7 | | |
| Z1.13 | 7.3 | 1.24 | 209.1 |
| Z5.1 | 6 | | |
| Z1.14 | 2.4 | | |
| Z5.10 | 2.4 | | |

TABLE 6

| | Through-cure, method 2 after 24 h [mm] | Through-cure, method 2 after 7 days [mm] | Breaking stress [N/mm²] | Elongation at break [%] |
|---|---|---|---|---|
| Z5.2 | 4 | 7 | 2.33 | 120.6 |
| Z5.3 | 4 | 19 | 2.49 | 185.4 |
| Z5.4 | 3 | 12 | 0.53 | 77.4 |

TP-1: Curable Polymer

Preparation as in EP 2 415 797 (US 2012/0029090) and alkoxylation as per EP 2 093 244 (US 2010/0041910) according to the following formula:

Preparation of alkoxylation products carrying alkoxysilyl groups by means of DMC catalysts by the method disclosed in EP 2 093 244. The epoxide oxygen content of the end products was determined in the presence of concentrated HCl on the principle of back-titration with aqueous sodium hydroxide solution.

A 5 litre autoclave is charged with 1412 g of polypropylene glycol (average molar mass 8000 g/mol) and 0.38 g of zinc hexacyanocobaltate-DMC catalyst, under nitrogen, and this initial charge is heated to 130° C. with stirring. The reactor is evacuated down to an internal pressure of 30 mbar, in order to effect distillative removal of any volatile ingredients present. A small amount of propylene oxide is added in order to activate the DMC catalyst, and, after 15 minutes and onset of the reaction, a further 706 g of propylene oxide are fed in at 130° C., with cooling, within 50 minutes. Subsequently, at the same time, 123 g of 3-glycidyloxypropyltriethoxysilane (DYNASYLAN® GLYEO) and 760 g of propylene oxide are metered in continuously and with cooling over the course of 1.5 hours at 100° C. The subsequent 90-minute reaction at 100° C. is followed by the degassing stage. The completed alkoxylation product is cooled to below 80° C. and discharged from the reactor.

The resulting alkoxylation product contains on average per molecule 2.5 trialkoxysilyl units and has an average molar mass of 17 000 g/mol. Free epoxide groups are not detectable in the end product. The viscosity of the alkoxylation product, determined using a calibrated rheometer, is about 13-17 Pa*s at 25° C. under a shear rate of 10 1/s.

TP-2: Curable Polymer

The same as for TP-1, with the following changes: The starter alcohol had an average molar mass Mn of 2000 g/mol and was used in the same amount in the same reactor. Catalyst activation was followed by the metered addition of an equimolar mixture of ethylene oxide and propylene oxide at 130° C. up to a molar mass increase of 8000 g/mol, followed by metered addition of propylene oxide containing 5 mol % of 3-glycidyloxypropyltriethoxysilane (DYNASYLAN® GLYEO). The polyether had an average molar mass of 15 000 g/mol and had 4 trialkoxysilyl units on average. Thereafter the polyether was reacted with equimolar amounts (based on the theoretical functionality and on the above-indicated metering amounts of the polyether) of isophorone diisocyanate, with addition of 60 ppm of dioctyltin dilaurate at 80° C. After half an hour, the reaction was stopped by addition of a mono-hydroxy-functional polyether (PPG prepared starting from butanol, Mn 400 g/mol). The mixture was stirred for a further hour at 80° C.

The product has a viscosity of 45 000 mPas and is colourless and clear.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the invention as defined in the following claims.

The invention claimed is:

1. A compound having guanidine groups and containing semi-organic silicon groups, of the formula (I):

$$M_a M^G_b D_c D^G_d T_e Q_f \quad (I);$$

where:
a = 0 to 10;
b = 0 to 10;
c = 0 to 350;
d = 0 to 50;
e = 0 to 50;
f = 0 to 10;
where the sum of the indices b and d is greater than or equal to 1 to 20;
with the proviso that:
when the index a is 2 and at the same time the sum of the indices b, c, e, and f is zero, the index d is other than 1; or
when the sum of the indices a, c, d, e, and f is zero, the index b is 2; and
where:
$M = [R_3SiO_{1/2}]$;
$M^G = [R^G R_2 SiO_{1/2}]$;
$D = [R_2 SiO_{2/2}]$;
$D^G = [R^G_2 SiO_{2/2}]$;
$T = [RSiO_{3/2}]$;
$Q = [SiO_{4/2}]$;
R are, independently of one another, identical or different and are $OR^a$ groups and/or linear or branched, saturated or else mono- or polyunsaturated hydrocarbon radicals, which may be interrupted by heteroatoms and/or may be substituted one or more times by hydroxyl, amino, carboxyl or aryl radicals;
where $R^a$ is identical or different and is hydrogen and/or alkyl groups having 1 to 12 carbon atoms; and
$R^G$ is a radical containing guanidine groups and selected from the group consisting of the formulas (IIa), (IIb), and (IIc), and tautomers and salts thereof:

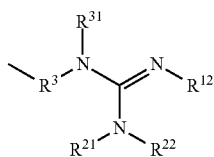

formula (IIa)

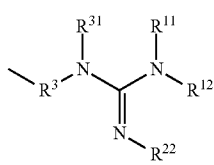

formula (IIb)

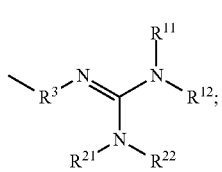

formula (IIc)

where:
R³ are divalent radicals which, independently of one another, are identical or different, linear or branched hydrocarbon radicals containing 1 to 50 carbon atoms, and may be interrupted by heteroatoms, and/or which may be substituted one or more times by hydroxyl or amino radicals; and R¹¹, R¹², R²¹, R²², and R³¹ are, independently of one another, identical or different and are hydrogen, linear or branched or cyclic hydrocarbons containing 1 to 15 carbon atoms, it being possible for the hydrocarbons also to contain 1 or 2 heteroatoms, preferred heteroatoms being nitrogen, oxygen and silicon;

wherein at least one $R^G$ in the formula (I) is of the formula (IIa) or (IIb).

2. The compound according to claim 1;
wherein:
the sum of the indices a, c, d, e and f is zero; and
the index b is 2.

3. The compound according to claim 1;
wherein the index d is 1 to 4.

4. A method comprising:
utilizing compounds having guanidine groups and containing semi-organic silicon groups according to claim 1 to cure compounds containing alkoxysilyl groups.

5. The method according to claim 4;
wherein the compound containing alkoxysilyl groups are polymers of the formula (III):

where:
P may be any desired polymer;
X is an alkoxy radical having 1 to 8 carbon atoms;
Y is an alkyl radical;
w is an index from 1 to 3; and
p is 1 to 100.

6. A compound having guanidine groups and containing semi-organic silicon groups, of the formula (I):

$$M_a M^G_b D_c D^G_d T_e Q_f \qquad (I);$$

where:
a = 0;
b = 0;
c 0 to 7;
d = 1 to 8;
e = 0;
f = 0;
wherein the sum of the indices c + d is from 3 to 8;
where:
D = [R₂SiO₂/₂];
$D^G = [R^G_2 SiO_{2/2}]$;
R is an OR$^a$ group, or a linear or branched, saturated or else mono- or polyunsaturated hydrocarbon radical, which may be interrupted by heteroatoms and/or may be substituted one or more times by hydroxyl, amino, carboxyl, or aryl radicals;
where R$^a$ is hydrogen or an alkyl group having 1 to 12 carbon atoms; and
$R^G$ is a radical containing guanidine groups and selected from the group consisting of the formulas (IIa), (IIb), and (IIc), and tautomers and salts thereof:

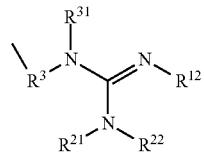

formula (IIa)

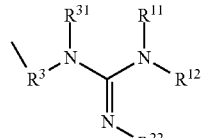

formula (IIb)

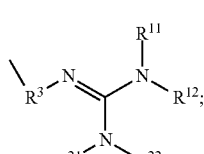

formula (IIc)

where:
R³ are divalent radicals which, independently of one another, are identical or different, linear or branched hydrocarbon radicals containing 1 to 50 carbon atoms, and may be interrupted by heteroatoms, and/or which may be substituted one or more times by hydroxyl or amino radicals; and R¹¹, R¹², R²¹, R²², and R³¹ are, independently of one another, identical or different and are hydrogen, linear or branched or cyclic hydrocarbons containing 1 to 15 carbon atoms, it being possible for the hydrocarbons also to contain 1 or 2 heteroatoms, preferred heteroatoms being nitrogen, oxygen and silicon.

7. A composition comprising:
(a) at least one compound having guanidine groups and containing semi-organic silicon groups; and
(b) at least one compound containing alkoxysilyl groups of the formula (III):

where:
P may be any desired polymer;
X is an alkoxy radical having 1 to 8 carbon atoms;
Y is an alkyl radical;
w is an index from 1 to 3 and
p is 1 to 100;
wherein the polymers of formula (III) containing alkoxysilyl groups comprise oxypropylene units.

8. The composition according to claim 7;
wherein the compounds of (a) are silanes and/or siloxanes having guanidine groups.

9. The composition according to claim 8, further comprising:
additives as well as the components (a) and (b).

10. The composition according to claim 7;
wherein the siloxanes of (a) are compounds having guanidine groups and containing semi-organic silicon groups of the formula (I):

wherein:
a = 0 to 10;
b = 0 to 10;
c = 0 to 350;

d =0 to 50;
e =0 to 50;
f =0 to 10;
where the sum of the indices b and d is greater than or equal to 1 to 20;
with the proviso that:
when the index a is 2 and at the same time the sum of the indices b, c, e, and f is zero, the index d is other than 1; or
when the sum of the indices a, c, d, e, and f is zero, the index b is greater than 1; and
wherein:
M=[$R_3SiO_{1/2}$];
$M^G$=[$R^G R_2 SiO_{1/2}$];
D=[$R_2SiO_{2/2}$];
$D^G$=[$R^G{}_2 SiO_{2/2}$];
T=[$RSiO_{3/2}$];
Q=[$SiO_{4/2}$];
R are, independently of one another, identical or different and are $OR^a$ groups and/or linear or branched, saturated or else mono- or polyunsaturated hydrocarbon radicals, which may be interrupted by heteroatoms and/or may be substituted one or more times by hydroxyl, amino, carboxyl or aryl radicals;
where $R^a$ is identical or different and is hydrogen and/or alkyl groups having 1 to 12 carbon atoms; and
$R^G$ is a radical containing guanidine groups and selected from the group consisting of the formulas (IIa), (IIb), and (IIc), and tautomers and salts thereof:

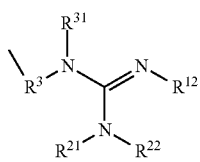

formula (IIa)

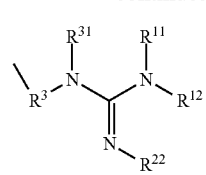

formula (IIb)

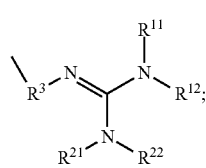

formula (IIc)

where:
$R^3$ are divalent radicals which, independently of one another, are identical or different, linear or branched hydrocarbon radicals containing 1 to 50 carbon atoms, and may be interrupted by heteroatoms, and/or which may be substituted one or more times by hydroxyl or amino radicals; and
$R^{11}$, $R^{12}$, $R^{21}$, $R^{22}$, and $R^{31}$ are, independently of one another, identical or different and are hydrogen, linear or branched or cyclic hydrocarbons containing 1 to 15 carbon atoms, it being possible for the hydrocarbons also to contain 1 or 2 heteroatoms, preferred heteroatoms being nitrogen, oxygen and silicon.

11. An adhesive or sealant comprising: the composition according to claim 7.

12. A coating material comprising: the composition according to claim 7.

13. A method comprising:
utilizing at least one compound according to claim 1 to cure compounds containing alkoxysilyl groups by forming Si—O—Si bonds.

14. The method according to claim 13;
wherein the curing of compounds containing alkoxysilyl groups is carried out at room temperature.

15. The method according to claim 14;
wherein the curing does not require metal catalysts.

* * * * *